United States Patent [19]

Engel et al.

[11] Patent Number: 4,550,107

[45] Date of Patent: Oct. 29, 1985

[54] CONDENSED DIAZEPINONES, THEIR COMPOSITIONS AND METHODS OF USE AS PHARMACEUTICALS

[75] Inventors: Wolfhard Engel, Biberach; Günter Trummlitz, Warthausen; Wolfgang Eberlein, Biberach; Gerhard Mihm, Biberach; Günther Schmidt, Biberach; Rüdolf Hammer, Ingelheim am Rhein, all of Fed. Rep. of Germany; Antonio Giachetti, Milan, Italy

[73] Assignee: Dr. Karl Thomae GmbH, Biberach an der Riss, Fed. Rep. of Germany

[21] Appl. No.: 711,913

[22] Filed: Mar. 14, 1985

[30] Foreign Application Priority Data

Mar. 14, 1984 [DE] Fed. Rep. of Germany ....... 3409237

[51] Int. Cl.[4] .................... A61K 31/55; C07D 521/00
[52] U.S. Cl. ................ 514/220; 260/239.3 T;
514/210; 546/246; 546/208; 546/193; 546/229;
546/329; 546/281; 546/334; 546/186; 544/360;
544/124; 544/372; 544/141; 548/518; 548/556;
260/239 B; 260/239.3 R
[58] Field of Search ................ 260/239.3 T; 514/210,
514/220

[56] References Cited

U.S. PATENT DOCUMENTS 4,443,452  4/1984  Engel et al. ................ 260/239.3 T Primary Examiner—Robert T. Bond
Attorney, Agent, or Firm—Charles J. Herron; David E. Frankhouser; Alan R. Stempel

[57] ABSTRACT

Disclosed are novel condensed diazepinones of formula I

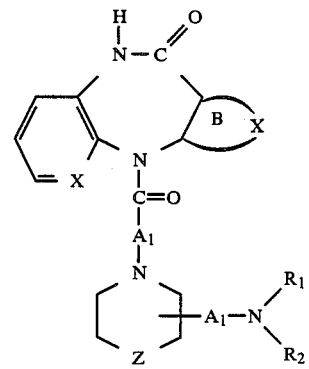

wherein B is a fused ring selected from

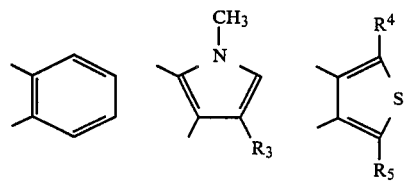

X is —CH— or, when B is ortho-phenylene, X can also be nitrogen; $A_1$ is $C_1$–$C_2$ alkylene; $A_2$ is $C_1$–$C_2$ when it is in the 2-position relative to the saturated heterocyclic ring nitrogen or a single bond or methylene when it is in the 3- or 4-position; $R_1$ is $C_1$–$C_3$ alkyl; $R_2$ is $C_1$–$C_7$ alkyl, optionally hydroxy-substituted on at least one of its second to seventh carbon, or $C_3$–$C_7$ cycloalkyl, optionally hydroxy substituted, or $C_3$–$C_7$ cycloalkylmethyl; or $R_1$ and $R_2$ can, together with the nitrogen therebetween, be a 4- to 7-membered saturated monocyclic, heterocyclic ring which can optionally include an oxygen or N—$CH_3$; $R_3$ is hydrogen, chlorine, or methyl; $R_4$ is hydrogen or $C_1$–$C_4$ alkyl, $R_5$ is hydrogen, chlorine or $C_1$–$C_4$ alkyl; and Z is a single bond, oxygen, methylene or 1,2-ethylene; and $NR_1R_2$—N oxides and non-toxic, pharmaceutically acceptable addition salts thereof. Also disclosed are pyrrolobenzodiazepinone intermediates, pharmaceutical compositions containing the condensed diazepinones and methods of using them to treat cardiovascular disorders, particularly bradycardia and bradyarrhythmia.

11 Claims, No Drawings

CONDENSED DIAZEPINONES, THEIR COMPOSITIONS AND METHODS OF USE AS PHARMACEUTICALS

BACKGROUND OF THE INVENTION

1. Field of the Invention

The invention relates to new condensed diazepinones, pyrrolobenzodiazepinone intermediates, pharmaceutical compositions containing the condensed diazepinones and methods of using them to treat cardiovascular disorders.

2. Brief Description of Prior Art

Condensed diazepinones, with anti-ulcer properties and an inhibitory effect on the secretion of gastric juices are already known from EP-A-O 039 519 and 0 057 428 and from U.S. Pat. Nos. 3,660,380; 3,691,159; 4,213,984; 4,213,985; 4,210,648; 4,110,527; 4,424,225; 4,424,222 and 4,424,226.

SUMMARY OF THE INVENTION

It has now been found that the diazepinones according to the present invention, possessing new aminoacyl groups, have valuable pharmacological properties which are suprisingly completely different from those of the compounds in the above mentioned publications.

The new condensed diazepinones are as shown in formula I (I)

wherein B is a fused ring selected from:

X is —CH— or, when B is ortho-phenylene, it can alternatively be nitrogen;

$A_1$ is $C_1$-$C_2$ alkylene;

$A_2$ is $C_1$-$C_2$ alkylene when it is in the 2-position relative to the saturated heterocyclic ring nitrogen or a single bond or methylene when it is in the 3- or 4-position;

$R_1$ if $C_1$-$C_3$ alkyl;

$R_2$ is $C_1$-$C_7$ alkyl, optionally hydroxy-substituted on at least one of its second to seventh carbon, or $C_3$-$C_7$ cycloalkyl, optionally hydroxy substituted, or $C_3$-$C_7$ cycloalkylmethyl; or $R_1$ and $R_2$ can, together with the nitrogen therebetween, be a 4- to 7- membered saturated, monocyclic, heterocyclic ring which can optionally include an oxygen or N—$CH_3$;

$R_3$ is hydrogen, chlorine or methyl;

$R_4$ is hydrogen or $C_1$-$C_4$ alkyl;

$R_5$ is hydrogen, chlorine or $C_1$-$C_4$ alkyl; and

Z is a single bond, oxygen, methylene or 1,2-ethylene; and $NR_1R_2$—N oxides and nontoxic, pharmaceutically acceptable addition salts thereof.

In one subgeneric aspect, the invention includes dibenzodiazepinone compounds of the formula In another subgeneric aspect, the invention includes pyridobenzodiazepinone compounds of the formula In yet another subgeneric aspect, the invention includes pyrrolobenzodiazepinone compounds of the formula In another subgeneric aspect, the invention includes thienobenzodiazepinone compounds of the formula

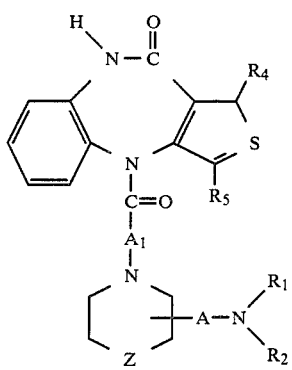

As noted, the compounds of general formula I and their $NR_1R_2$—N—oxides can also occur in the form of their nontoxic, pharmaceutically acceptable acid addition salts. Suitable acids include, for example, hydrochloric, hydrobromic, sulfuric, methylsulfuric, phosphoric, tartaric, fumaric, citric, maleic, succinic, gluconic, malic, p-toluenesulfonic, methanesulfonic or amidosulfonic acid.

The invention further relates to new pyrrolobenzodiazepinones of formula Ia

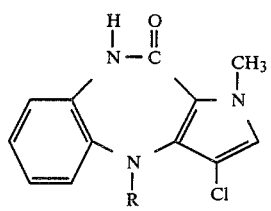

which are used as intermediates, wherein R represents a hydrogen atom or a haloacyl group, preferably a chloroacyl group, with a total of 2 or 3 carbon atoms.

DETAILED DESCRIPTION OF THE INVENTION

According to the invention, the new base-substituted condensed diazepinones of general formula I are obtained by the following processes:

Process A

Base-substituted condensed diazepinones (I) wherein $R_3$ is methyl or chlorine and B, X, $A_1$, $A_2$, $R_1$, $R_2$, $R_4$, $R_5$ and Z are as above defined are obtained by reacting haloacyl coupounds wherein Hal is chlorine, bromine or iodine, with secondary amines of formula (III) as follows:

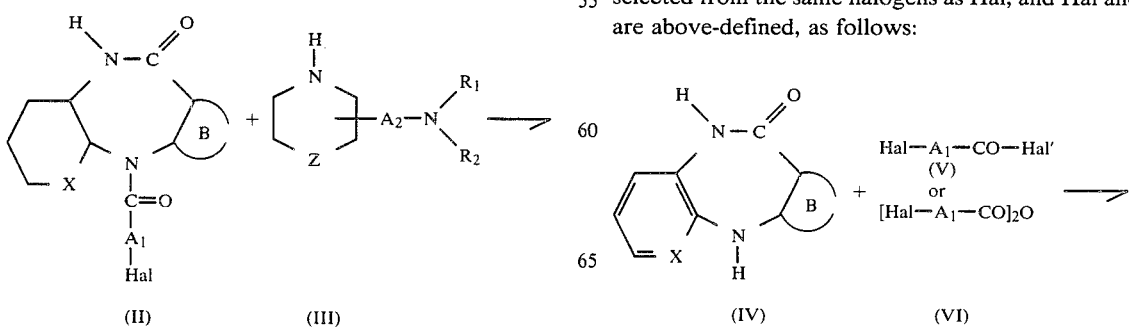

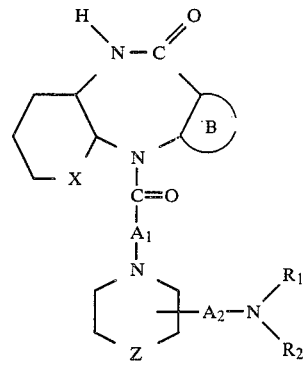

Amination is carried out in an inert solvent at temperatures of between $-10°$ C. and the boiling temperature of the solvent, preferably either with at least 2 moles of secondary amine (III) or with 1 to 2 moles of a secondary amine (III) and of an auxiliary base. The solvents used can be, for example, chlorinated hydrocarbons such as methylene chloride, chloroform or dichloroethane; open-chain or cyclic ethers such as diethyl ether, tetrahydrofuran or dioxan; aromatic hydrocarbons such as benzene, toluene, xylene, chlorobenzene or pyridine; alcohols such as ethanol or isopropanol; ketones such as acetone; acetonitrile or dimethylformamide. The auxiliary bases used can be, for example, tertiary organic bases such as triethylamine, N-methylpiperidine, diethylaniline, pyridine and 4-(dimethylamino)pyridine or inorganic bases such as alkali metal or alkaline earth metal carbonates or hydrogen carbonates, hydroxides or oxides. If desired, the reaction can be accelerated by the addition of alkali metal iodides. The reaction times are between 15 minutes and 18 hours depending on the nature and the quantity of the amine (III) used.

In the reacton of haloacyl compound (II) wherein $A_1$ is an ethylene group, H-Hal can also be split off during the reaction; the acryloyl compounds formed as intermediates and capable of isolation react with the secondary amine (III) to form the same end product (I).

In order to prepare the above haloacyl compounds (II), compounds of formula IV, wherein B is as previously defined, can be reacted with acid halides (V) or acid anhydrides (VII) wherein Hal is independently selected from the same halogens as Hal, and Hal and $A_1$ are above-defined, as follows:

-continued

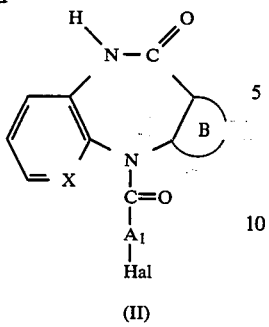

(II)

This acylation can be carried out without or preferably in an inert solvent at ambient temperature or elevated temperature, at most at the boiling temperature of the solvent, optionally in the presence of an auxiliary base and/or an acylation catalyst. The acid halides (V) are preferred to the acid anhydrides (VI). Chloroacetyl chloride is preferred as the acid halide (V) and chloroacetic acid anhydride is preferred as the acid anhydride (VI). Examples of solvents include aromatic hydrocarbons such as toluene, xylene and chlorobenzene; openchain or cyclic ethers such as diisopropyl ether and dioxan; chlorinated hydrocarbons such as dichloroethane and other solvents such as pyridine, acetonitrile and dimethylformamide.

Examples of the auxiliary bases which can be used include tertiary organic bases such as triethylamine, ethyl diisopropylamine and pyridine; and inorganic bases such as anhydrous alkali metal and alkaline earth metal carbonates and hydrogen carbonates and alkaline earth metal oxides. The acylating catalysts used can be, for example, imidazole, pyridine or 4-dimethylaminopyridine.

If, in a haloacyl (II), Hal represents a chlorine atom, it can readily be exchanged for the more reactive iodine by reaction with NaI in acetone or ethanol.

The compounds of formula IV which do not correspond to formula Ia(R=H), are already known, See EP-A 39,519; EP-A 57,428; DE-C 1,179,943 and 1,204,680; F. Hunzicker et. al., Arzneim.-Forsch. 13:324 (1963).

Secondary amines (III) wherein Z is methylene and $R_1$, $R_2$ and $A_2$ are as hereinbefore defined are already known or can be prepared analogously to known methods. Thus, for example, secondary amines (III) wherein $A_2$ represent a methylene group can be obtained by reacting 2-, 3-, or 4-(chloromethyl)pyridine hydrochloride with a secondary amine of formula VII

wherein $R_1$ and $R_2$ are as hereinbefore defined (analogously to A. Fischer et al., Can. J. Chem. 56:3059–3067 [1967]) and subsequent catalytic hydrogenation of the teriary picolylamine obtained, for example in ethanolic hydrochloric acid solution, using platinum (IV) oxide as catalyst (see also F. F. Blicke et al., J. Org. Chemistry 26, 3258[1961]) or in glacial acetic acid in the presence of platinum (IV) oxide (see also W. F. Minor et al., J. Med. Pharm. Chem. 5, 96, 105ff [1962] and A. H. Sommers et al., J. Amer. Chem. Soc., 75: 57–58ff. (1953). The 2-substituted piperidines, of formula IIIa, falling within general formula III, wherein $R_1$ and $R_2$ are as hereinbefore defined.

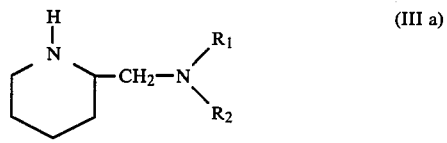

can also be prepared by reacting 2-(chloromethyl)-piperidine hydrochloride (T. R. Norton, R. A. Seibert, A. A. Benson and F. W. Bergstrom, J. Amer. Chem. Soc. 68, 1572–1576 [1946] and M. Rinle and H. G. Liem, Archiv der Pharmazie 292, 165–169 [1959]) with a secondary amine of formula VII. By-products of this reaction, which can be carried out analogously to the description by H. Biere and U. Redmann in Eur. J. Med. Chem. 11, 351–357 (1976), are generally the 3-substituted hexahydroazepines of general formula IIIb,

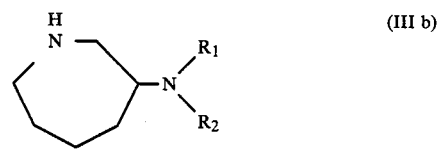

which are also covered by general formula III. IIIa and IIIb may easily be separated by conventional methods, e.g. by fractional distillation or fractional crystallisation of their salts, e.g. their dihydrochlorides.

The starting compounds of formula IIIc, falling within general formula III,

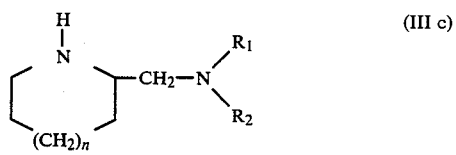

wherein $R_1$ and $R_2$ are as herinbefore defined and n is 1 or 2, can also be obtained as described by A. J. Schmid et al., Helv. Chim. Acta 39, 607–618 (1956) or analogously thereto.

Secondary amines (III) wherein Z is a methylene group, $A_2$ is 1,2-ethylene, $R_1$ and $R_2$ are as hereinbefore defined and the side chain is in the 2 position of the piperidine ring, can be obtained by the addition of amines of formula VII to 2-vinylpyridine (cf. also F. F. Bicke et al., J. Org. Chem. 26, 3257–3260[1961]; W. F. Minor et al., J. Med. Pharm. Chem. 5, 96–107[1962]; A. H. Sommers et al., J. Amer. Chem. Soc. 75, 57–60[1953]) and subsequent catalytic hydrogenation under the conditions specified hereinbefore.

The 2-[(dialkylamino)methyl]pyrrolidines, included among the secondary amines (III), wherein Z is a single bond, can be obtained in accordance with or analogously to T. Sone et al., Chem. Pharm. Bull. (Tokyo) 21, 2331[1973] by reduction of corresponding prolinamides with lithium aluminium hydride. If proline is replaced by hexahydro-1H-azepine-2-carboxylic acid in this synthesis (cf. H. T. Nagasawa et al., J. Med. Chem. 14, 501 [1971]), the 2-substituted hexahydro-1H-azepines covered by general formula III are obtained, where Z is ethylene group, $A_2$ is methylene group and $R_1$ and $R_2$ are as hereinbefore defined.

The 3-[(dialkylamino)methyl]piperidines, included among the secondary amines (III) can also be prepared from corresponding nicotinic acid amines according to V. M. Micovic et al., *J. Org. Chem.* 18, 1196 [1953] and F. Haglid et al., *Acta. Chem. Scand.* 17, 1741 [1963]. Hexahydronicotine is obtained from nicotine in accordance with the method described by W. R. Harlan and R. M. Hixon, *J. Amer. Chem. Soc.* 52, 3385–3388 (1930).

The 3-(dialkylamino-pyrrolidines, -piperidines and -hexahydro-1H-azepines (III) wherein $R_1$ and $R_2$ are as hereinbefore defined; Z is methylene, ethylene or a single bond; and $A_2$ is a single bond can be obtained in accordance with the method described by H. R. Burki et al., *Eur. J. Med. Chem.* 13, 479–485 [1978] and U.S. Pat. No. 3,980,788; C. A. 85:P182415z [1976] from N-benzyl-3-pyrrolidinone, -3-piperidinone or -hexahydro-1H-azepin-3-one or analogously thereto.

Secondary amines (III) wherein Z is oxygen and the group

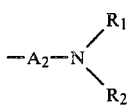

is in the 2 position relative to the secondary amino group, can be obtained from 3-oxomorpholine by N-benzylation, alkylation with dialkyl sulphates, condensation with nitromethane, transformation of the nitromethylene group by reduction or careful catalytic hydrogenation, transformation of the primary amino group, for example, by Eschweiler-Clarke methylation or reaction with suitable alkyl halides, dialkyl sulphates or α, ω-dihaloalkanes and finally hydrogenolytic splitting off of the protecting group.

Process B

Compounds of general formula I, as defined in Process A above, can also be obtained by acylating tricyclic compounds of Formula IV, as shown above, with carboxylic acid derivatives (VIII) wherein $R_1$, $R_2$, $A_1$, $A_2$ and Z are as hereinbefore defined and Nu is a leaving group, as follows:

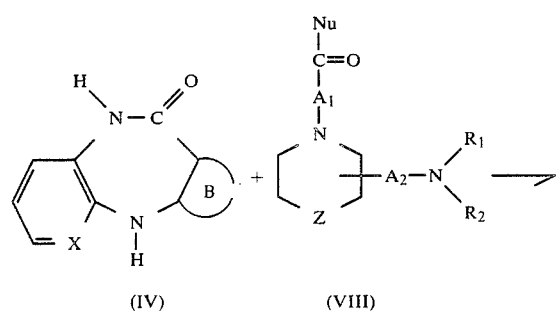

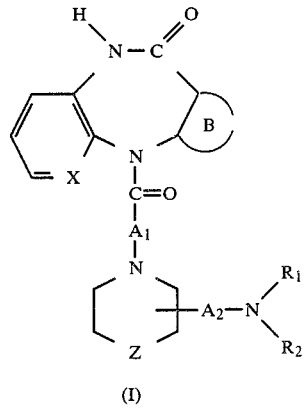

The compounds of formula IV are reacted with the carboxylic acid derivatives (VIII) in a manner known per se. The leaving group Nu is a group which forms, together with the carbonyl group to which it is bonded, a reactive carboxylic acid derivative. Examples of reactive carboxylic acid derivatives include acid halides, esters, anhydrides and mixed anhydrides such as those formed from salts of the corresponding acids (Nu=OH) and acid chlorides such as phosphorus oxychloride, diphosphoric acid tetrachloride or chloroformic acid esters, or the N-alkyl-2-acyloxypyridinium salts formed by reacting compounds of formula VIII (Nu=OH) with N-alkyl-2-halopyridinium salts.

The reaction is preferably carried out with the mixed anhydrides of strong inorganic acids, particularly dichlorophosphoric acid. The reaction is optionally carried out in the presence of an acid-binding agent (proton acceptor). Examples of suitable proton acceptors include alkali metal carbonates and hydrogen carbonates such as sodium carbonate and potassium hydrogen carbonate; tertiary organic amines such a pyridine, triethylamine, ethyldiisopropylamine, 4-(dimethylamino)pyridine, and sodium hydride. The reaction is carried out at temperatures of between −25° C. and 130° C. in an inert solvent. Examples of inert solvents include chlorinated aliphatic hydrocarbons such as methylene chloride and 1,2-dichloroethane; open-chain or cyclic ethers such as diethyl ether, tetrahydrofuran and 1,4-dioxan; aromatic hydrocarbons such as benzene, toluene, xylene and o-dichlorobezene; polar aprotic solvents such as acetonitrile, dimethylformamide and hexamethylphosphoric acid triamide; and mixtures thereof. The reaction times are between 15 minutes and 18 hours depending on the nature and quantity of the acylating agent of general formula VIII used. It is not necessary to prepare the compounds of general formula VIII in pure form; instead, they can be produced in situ in the reaction mixture in known manner.

The carboxylic acid derivatives (VIII) wherein Nu represents an alkoxy group can be obtained by reacting diamines (III) with haloacetic acid esters. β-halopropionic acid esters or acrylic esters, optionally using additional auxiliary bases, e.g. triethylamine, or catalysts, e.g. Triton B. By saponification of the resulting esters, e.g. with barium hydroxide solution, the carboxylic acids (VIII) are obtained, which can be used to prepare derivatives with other leaving groups.

Process C

The new pyrrolobenzodiazepinones falling within general formula I, wherein $R_1$, $R_2$, $A_1$, $A_2$ and Z are as hereinbefore defined and $R_3$ is hydrogen can be prepared by hydrogenolysis from corresponding compounds wherein $R_3$ is chlorine. The hydrogenolysis is carried out in the presence of catalysts consisting of metal from the VIIIth sub-group of the Periodic Table of elements, for example palladium on animal charcoal, palladium on barium sulfate. Raney nickel or Raney cobalt and at hydrogen pressures of from 1 to 300 bar and temperatures of from 0° C. in the presence of solvent, e.g. alcohols such as methanol or ethanol; ethers such as dioxan or tetrahydrofuran; carboxylic acids such as acetic acid; or tertiary amines, e.g. triethylamine. If the reaction is carried out in the absence of any additional hydrogen chloride acceptors, e.g. sodium carbonate, potassium hydrogen carbonate, triethylamine or sodium acetate, the hydrochlorides of the desired compounds are formed directly and can be isolated after removal of the catalyst by evaporation of the reaction solution. If the hydrogen is replaced by formic acid in the above mentioned hydrogenolysis reaction, the reaction will be successful in principle even when carried out not under pressure. In this alternative embodiment, reaction with formic acid in the presence of dimethylformamide as solvent and of palladium on charcoal as catalyst at temperatures of between 70° and 110° C. is successful, as is reduction with triethylammonium formate in the presence of excess triethylamine and palladium on animal charcoal or palladium acetate and triaryl phosphines such as triphenyl phosphines, tris-(o-tolyl)phosphine, and tris-(2,5-diisopropylphenyl)phosphine at temperatures between 40° and 110° C.

The compounds of general formula I thus obtained can subsequently optionally be converted into their $NR_1R_2$—N— oxides by oxidation with hydrogen peroxide or with peracids, for example with 3-chloro-perbenzoic acid. By this oxidation only the nitrogen atom of the side-chain —$A_2$—$NR_1R_2$ is oxidized.

Bases of formula I thus obtained can subsequently be converted into the acid addition salts thereof or, if the acid addition salts are obtained, these may be converted into the free bases or other pharmaceutically acceptable acid addition salts.

The base-substituted condensed diazepinones of formula I according to the invention contain up to two independent chiral elements, including an asymmetric carbon atom in the side chain. The second chiral element is the acylated tricyclic moiety itself, which can occur in two mirror-image forms. The nature of the tricyclic compound determines whether the energy barrier for inversion at this center is so high that the individual isomers are stable at ambient temperature and capable of being isolated. It has been found that those compounds of formula I wherein X is —CH— and B is o-phenylene, always occur in two diastereoisomeric forms which can be separated into their components at ambient temperature. The individual diastereoisomers are completely stable in the crystalline state but in solution and at ambient temperature they revert with half-life of a few days to the original mixture. In compounds of formula I wherein X is nitrogen and B is o-phenylene, the activating energy required is so sharply reduced that at ambient temperature, diastereoisomers can no longer be detected, except by comples $^1$H-NMR spectra, let alone preparatively resolved.

The aminoacylated condensed diazepinones of formula I according to the invention thus generally contain 2 chiral centers, one of which is, under certain circumstances, not of stable configuration at ambient temperature. These compounds may therefore occur in two diastereoisomeric forms or as enantiomeric (+) and (−) forms. The invention includes the individual isomers as well as mixtures thereof. The diastereoisomers can be separated on the basis of their different physico-chemical properties, e.g. by fractional recrystallization from suitable solvents, by high pressure liquid chromatography, by column chromatography or by gas chromatography.

The splitting of any racemates of the compounds of formula I can be carried out by known methods, for example using an optically active acid such as (+) or (−) tartaric acid or a derivative thereof such as (+) or (−) diacetyl tartaric acid, (+) or (−) monomethyl tartrate or (+) camphor sulphonic acid.

According to a conventional method of separting isomers, the racemate of a compound of formula I is reacted with one of the above-mentioned optically active acids in an equivalent quantity in a solvent and the resulting crystalline optically active salts are separated on the basis of their different solubilities. This reaction can be carried out in any type of solvent provided that the solvent gives a sufficiently different solubility for the salts. Preferably, methanol, ethanol or mixtures thereof are used, e.g. in a ratio by volume of 50:50. Then, each of the optically active salts is dissolved in water, neutralized with a base such as sodium carbonate or potassium carbonate and in this way the corresponding free compound is obtained in the (+) or (−) form.

Only one enantiomer or a mixture of two optically active diastereoisomeric compounds of formula I will be obtained if the methods of synthesis described above are carried out with only one enantiomer of formula III or VIII.

Process D

The new compound of formula Ia according to the invention wherein R is hydrogen, also required as an intermediate product, can be obtained by cyclising compounds of formula IX

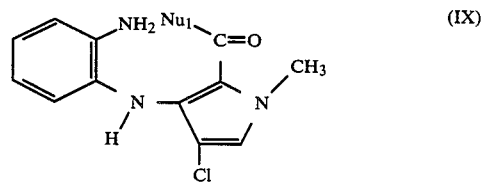

wherein $Nu_1$ is a suitable leaving group and subsequently, if desired, the resulting tricyclic compound of formula Ia, wherein R is hydrogen, is acylated using the methods given for the synthesis of compounds of formula II, thereby producing compounds of general formula Ia wherein R is haloacetyl or 3-halo-1-oxopropyl.

The cyclization of compounds of general formula IX is carried out in a manner known per se, depending on the nature of the leaving group $Nu_1$. Suitable leaving groups $Nu_1$ are groups which, together with the carbonyl group to which they are bonded, form a reactive carboxylic acid derivative. Examples of suitable leaving groups $Nu_1$ include alkoxy, amino and hydroxy groups.

If $Nu_1$ is an amino group, for example, the cyclization can be carried out without a solvent or in inert, preferably polar, organic solvents such as lower alcohols, e.g. ethanol, optionally in the presence of an acid such as a hydrohalic acid, or in the presence of a base such as an alkali metal alkoxide, at temperatures of between 0° C. and 200° C., preferably at the boiling temperature of the solvent used. If $Nu_1$ is an alkoxy group, the cyclization of compound IX can be carried out at temperatures of between 0° C. and 200° C., preferably between 20° and 120° C., without a solvent or in the presence of an inert solvent, optionally in the presence of a basic or preferably acidic catalyst. The reaction times are from 15 minutes to 6 hours. Suitable solvents include, for example, alcohols such as ethanol, isopropanol and glycol; ethers such as dioxan and diphenyl ether; aromatic hydrocarbons such as toluene, xylene and o-dichlorobenzene; and dimethylsulphoxide. However, the reaction can also be carried out in the absence of any additional solvents.

Examples of suitable catalysts include basic catalysts such as alkali metal alkoxides, e.g. sodium methoxide, potassium tertbutoxide, n-butyllithium and sodium hydride; and acidic catalysts such as organic or inorganic acids, e.g. acetic, chloroacetic, p-toluenesulphonic, o-chlorobenzoic, p-toluic, nicotinic, trifluoroacetic, fumaric, hydrochloric and benzoic acids, potassium hydrogen sulphate or preferably phosphoric acid. If necessary, several moles of acidic catalyst may be used per mol of starting compound.

If $Nu_1$ is a hydroxy group, the cyclization of compound IX can be carried out, for example, in polar solvents, preferably with acidic catalysis and advantageously in the presence of a condensing agent such as N,N'-dicyclohexylcarbodiimide, or with continuous separation of the water formed during the reaction, e.g. by azeotropic removal of the water using a water separator. The reaction is preferably carried out at temperatures of between 50° C. and 200° C., more particularly at temperatures of between 50° C. and 160° C.

Compounds of formula IX can be obtained by reacting o-halo-nitrobenzenes (X), preferably 2-fluoro-nitrobenzene, with 3-aminopyrroles (XI), as follows:

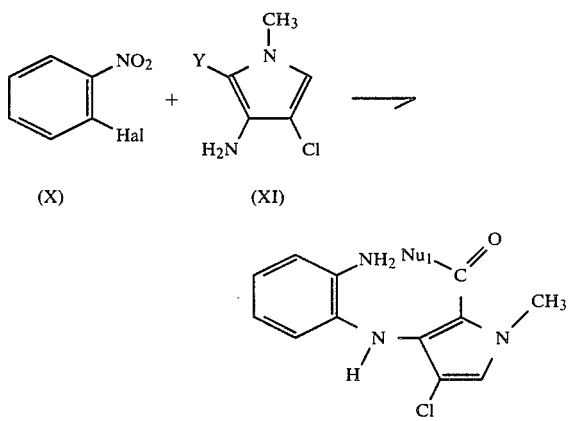

wherein in formula X Hal is halogen atom, particularly fluorine or chlorine, and Y is $Nu_1$—CO— or the precursor of an $Nu_1$—CO— group), subsequent reduction of the nitro group to form the amino group and optionally subsequent conversion of Y into a suitable group $Nu_1$—CO—. The term "precursor of an $Nu_1$—CO— group" means a substituent which can be converted into the $Nu_1$—CO— group by a suitable procedure with which one skilled in the art would be familiar (e.g. hydrolysis, alcoholysis, acidification, saponification, etc.). Preferred precursors are the nitrile group (—CN) and the carboxylate group (—COO—), which can be converted into the amide, ester or carboxylic acid group by hydrolysis, alcoholysis or acidification.

The reaction of the o-halo-nitrobenzenes (X) with the 3-aminopyrroles (XI) is carried out in a manner known per se, preferably with the addition of a deprotonating agent, e.g. potassium tert.butoxide, sodium hydride, potassium carbonate or a tertiary amine, in solvents such as dimethylformamide, dioxan, tetrahydrofuran or N-methylpyrrolidone, at temperatures of between 0° C. and 150° C. depending on the nature of the Hal group and on the nature of the deprotonating agent used.

The reduction of the nitro group to form the amino group is carried out by the methods conventionally used with aromatic nitro compounds or heterocyclic nitro compounds.

The 3-aminopyrroles (XI) can be prepared by cyclization of N-(2-chloro-2-cyano-ethenyl)-methylamino-acetic acid derivatives or acetonitriles in the presence of strong bases, e.g. potassium tert.butoxide, sodium methoxide or sodium hydride, and in suitable inert solvents, e.g. toluene, dimethylformamide or N-methylpyrrolidone. The aminopyrroles (IX) need not be isolated in pure form but can be reacted further (without working up the reaction solutions) in the same solvent with the halo-nitrobenzenes (X). The N-(2-chloro-2-cyano-ethenyl)methylamino-acetic acid derivatives, e.g. the corresponding methyl or ethyl esters, or acetonitriles, can be obtained by the addition of sarcosine esters or (methylamino)acetonitrile to 2,3-dichloroacrylonitrile. The 2,3-dichloroacrylonitrile need not be used as such but can be produced in situ from 2,2,3-trichloropropionitrile in the presence of bases, e.g. triethylamine. The 2,2,3-trichloropropionitrile is in turn produced, contrary to the conflicting information in U.S. Pat. No. 3,161,577; C.A. 62, 6399d[1965], as the single product in the photochlorination of 3-chloropropionitrile.

The invention further relates to pharmaceutical compositions containing one or more condensed diazepinones of general formula I or the physiologically acceptable salts thereof. For this purpose, the compounds of general formula I can be incorporated in known manner in conventional pharmaceutical preparations, e.g. solution, suppositories, plain tablets, coated tablets, capsules or infusions. The daily dose is generally 0.02 to 5 mg, preferably 0.02 to 2.5 mg, more particularly 0.05 to 1.0 mg/kg of body weight, which can be administered in several, preferably 1 to 3 dosage units, in order to obtain the desired results.

The base-substituted condensed diazepinones (I) and the acid addition salts thereof have valuable properties; in particular, they have favorable effects on heart rate and in view of the absence of inhibitory effects on the secretion of gastric acid, inhibitory effects on salivation and mydriatic effects, they are suitable as vagal pacemakers for the treatment of bradycardia and bradyarrhythmia in human and veterinary medicine. Some of the compounds also have spasmolytic properties on peripheral organs, particularly the colon and bladder.

The Examples which follow illustrate the invention. In the Examples "Mp" indicates "melting point", and "D." indicates "decomposition". Satisfactory elementary analyses, IR, UV and $^1$H-NMR and in some cases mass spectra as well have been obtained for all the compounds.

PREPARATION OF THE STARTING MATERIAL

EXAMPLE A

2-[(1-Pyrrolidinyl)methyl]pyridine

With stirring and external cooling with ice, a solution of 2-(chloromethyl)pyridine hydrochloride (100 g, 0.61 mol) in 95% ethanol (600 ml) is added dropwise to pyrrolidine (500 ml, 426 g, 5.99 mol) and the resulting mixture is heated to 90° C. for 1 hour. After cooling, the mixture is suction filtered, the filter residue is thoroughly washed with ether, the filtrate is concentrated in vacuo and the residue is made strongly alkaline with 40% potassium hydroxide solution. It is extracted exhaustively with ether, the extracts obtained are freed from solvent and the remaining residue is distilled in vacuo. The desired compound (93.0 g) is obtained. Boiling point $_{19\ mm\ Hg}$ 118°–121° C.

The following are prepared analogously:
2-[(Dimethylamino)methyl]pyridine, boiling point $_{0.3\ mm\ Hg}$ 30° C.;
2-[(Diethylamino)methyl]pyridine, boiling point $_{20\ mm\ Hg}$ 104°–106° C.;
2-[(4-Morpholinyl)methyl]pyridine, boiling point $_{4\ mm\ Hg}$ 106°–107° C.;
2-[[(Cyclohexyl)(methyl)amino]methyl]-pyridine, boiling point $_{4\ mm\ Hg}$ 108°–110° C.;
2-[(1-Piperidinyl)methyl]pyridine, boiling point $_{20\ mm\ Hg}$ 125°–130° C.;
2-[(4-Methyl-1-piperazinyl)methyl]pyridine, boiling point $_{18\ mm\ Hg}$ 148°–153° C.;
Melting point of the monohydrochloride 175°–176° C.;
trans-2-[[4-hydroxycyclohexyl)(methyl)amino]methyl]-pyridine, R$_F$ 0.58 (Polygram SIL G/UV 254 [Macherey-Nagel]: Eluant: methylene chloride/methanol/cyclohexane/concentrated ammonia=68:15:15:2).
3-[[(Cyclohexyl)(methyl)amino]methyl]pyridine, boiling point $_{10\ mm\ Hg}$ 148°–153° C.;
3-[(Dimethylamino)methyl]pyridine, boiling point $_{10\ mm\ Hg}$ 82° C.;
3-[(1-Pyrrolidinyl)methyl]pyridine, boiling point $_{11\ mm\ Hg}$ 122°–125° C.;
3-[(1-Piperidinyl)methyl]pyridine, boiling point $_{11\ mm\ Hg}$ 128°–130° C.;
3-[(Diethylamino)methyl]pyridine, boiling point $_{14\ mm\ Hg}$ 108°–109° C.;
2-[[(2-Hydroxyethyl)(methyl)amino]methyl]pyridine, boiling point $_{18\ mm\ Hg}$ 162° C.;
2-[(Butylmethylamino)methyl]pyridine, boiling point $_{20\ mm\ Hg}$ 109°–110° C.;
2-[(Ethylmethylamino)methyl]pyridine, boiling point $_{17\ mm\ Hg}$ 86° C.

EXAMPLE B

2-[(4-Morpholinyl)methyl]piperidine

First, 2-[(4-morpholinyl)methyl]pyridine (94.0 g, 0.53 mol) is dissolved in glacial acetic acid (600 ml) and hydrogenated in the presence of platinum(IV) oxide (10.0 g) as catalyst for 2 hours at a hydrogen pressure of 3 bar and a temperature of 50° C. After cooling, the catalyst is filtered off, the filtrate is freed from solvent and the residue is distilled in vacuo. The desired compound (51.0 g) is obtained in the form of a colorless liquid, boiling point $_{4\ mm\ Hg}$ 91°–92° C.

The following are prepared analogously:
2-[(Dimethylamino)methyl]piperidine boiling point $_{15\ mm\ Hg}$ 71°–75° C.;
2-[(Diethylamino)methyl]piperdine, boiling point $_{17\ mm\ Hg}$ 88°–94° C.;
2-[2[(Dimethylamino)ethyl]]piperidine, boiling point $_{28\ mm\ Hg}$ 102°–106° C.;
2-[2-(Dimethylamino)ethyl]]piperidine, boiling point $_{20\ mm\ Hg}$ 118°–120° C.;
2-[(1-Pyrrolidinyl)methyl]piperdine, boiling point $_{20\ mm\ Hg}$ 115° C.;
2-[[(Cyclohexyl)(methyl)amino]methyl]piperdine, boiling point $_{4\ mm\ Hg}$ 103°–108° C.;
2-[(1-Piperidinyl)methyl]piperidine, boiling point $_{18\ mm\ Hg}$ 115°–125° C.;
2-[(4-Methyl-1-piperazinyl)methyl]piperidine, boiling point $_{18\ mm\ Hg}$ 142°–145° C.; N$_D^{20}$ 1.4959;
trans-2-[[(4-Hydroxycyclohexyl)(methyl)amino]methyl]-piperidine, R$_F$ 0.55 (Polygram SIL G/UV$_{254}$ [Macherey-Nagel]: eluant is dichloromethane/methanol/cyclohexane/conc. ammonia=68:15:15:2). Mp. 58°–60° C.;
2-[[(2-Hydroxyethyl)(methyl)amino]methyl]piperidine, boiling point $_{18\ mm\ Hg}$ 144°–146° C.;
2-[(Butylmethylamino)methyl]piperidine, boiling point $_{20\ mm\ Hg}$ 115° C.;
2-[(Ethylmethylamino)methyl]piperidine, boiling point $_{18\ mm\ Hg}$ 79°–80° C.;
3-[[(Cyclohexyl)(methyl)amino]methyl]piperidine, boiling point $_{11\ mm\ Hg}$ 139°–153° C.;
3-[(Dimethylamino)methyl]piperidine, boiling point $_{12\ mm\ Hg}$ 74°–75° C.;
3-[(1-Pyrrolidinyl)methyl]piperidine, boiling point $_{13\ mm\ Hg}$ 123°–124° C.;
3-[(1-Piperidinyl)methyl]piperidine, boiling point $_{23\ mm\ Hg}$ 141°–145° C.;
3-[(Diethylamino)methyl]piperidine, boiling point $_{12\ mm\ Hg}$ 106°–108° C.;

EXAMPLE C (S)-2-[(1-Pyrrolidinyl)methyl]pyrrolidine (a)

(S)-1-[[1-[[(Phenylmethyl)oxy]carbonyl]-2-pyrrolidinyl]carbonyl]-pyrrolidine

A mixture of N-carbobenzoxy-L-proline (30.0 g. 0.12 mol), anhydrous tetrahydrofuran (200 ml) and thionyl chloride (20 ml, 0.257 mol) is refluxed for 2 hours and then concentrated under water jet vacuum. The oily residue is taken up in anhydrous tetrahydrofuran (200 ml) and, with external cooling with water, a solution of pyrrolidine (41.8 ml, 0.5 mol) in tetrahydrofuran (200 ml) is added dropwise thereto. After 2 hours boiling, the solvent is evaporated off, the residue is mixed with excess saturated aqueous potassium carbonate solution and extracted exhaustively with ethyl acetate. The combined extracts are dried over sodium sulphate and concentrated and the colourless residue remaining is recrystallized from acetone/petroleum ether (3:1 v/v). Colorless crystals (26.0 g) are obtained, m.p. 138° C.

The following are prepared analogously:
(S)-N,N-Diethyl-1-[[(phenylmethyl)oxy]carbonyl]-prolinamide, yellow oil;
(S)-4-Methyl-1-[[(phenylmethyl)oxy]carbonyl]-2-pyrrolidinyl]-carbonyl]-piperazine, m.p. 95°–96° C.

(b) (S)-1-[(2-Pyrrolidinyl)carbonyl]-pyrrolidine (S)-1-[[1-[[(Phenylmethyl)oxy]carbonyl]-2-pyrrolidinyl]-carbonyl]-pyrrolidine (18.6 g, 0.0615 mol) is dissolved in ethanol (100 ml) and, after the addition of 5% palladium/animal charcoal catalyst (1.0 g), hydrogenated at ambient temperature under 1 bar of hydrogen pressure until the reaction has ended. The mixture is filtered and the filtrate is concentred in vacuo. The residue is distilled in vacuo. A colorless oil (8.4 g) is obtained, boiling point $_{4\ mm\ Hg}$ 134°–136° C.

The following are prepared analogously:
(S)-N,N-Diethyl-prolinamide, boiling point 5 mm Hg 107°–108° C.;
(S)-4-methyl-1-[(2-pyrrolidinyl)carbonyl]-piperazine, oil.

(c) (S)-2-[(1-Pyrrolidinyl)methyl]pyrrolidine

An anhydrous solution of (S)-1-[(2-pyrrolidinyl)carbonyl]-pyrrolidine (21.87 g. 0.13 mol) in anhydrous tetrahydrofuran (100 ml) is added dropwise, with stirring and external cooling with ice, to a suspension of lithium aluminium hydride (7.4 g, 0.2 mol) in dry tetrahydrofuran (200 ml). The mixture is then refluxed for 18 hours, left to cool and the excess complex hydride is decomposed by the addition of water (7 ml), followed by 15% sodium hydroxide solution (7 ml) and finally water (15/ml). After tetrahydrofuran (100 ml) has been added, the mixture is refluxed for a further 30 minutes, left to cool and then dried by the addition of substantially anhydrous potassium carbonate. It is then filltered, the filtrate is concentrated in vacuo and the oily residue is distilled under reduced pressure. A colorless oil (16.6 g) is obtained, boiling point $_{12\ mm\ Hg}$ 95°–98° C. $[\alpha]_D^{20}+4.45°$(ethanol).

The following are prepared analogously:
(S)-2-[(Diethylamino)methyl]pyrrolidine, boiling point $_{30\ mm\ Hg}$ 100°–105° C., $[\alpha]_D^{20}+11.3°$(ethanol) [Lit.-:$[\alpha]_D^{20}+13.4°$(ethanol)];
(S)-4-Methyl-1-[(2-pyrrolidinyl)methyl]piperazine, boiling point $_{12\ mm\ Hg}$ 125° C. $[\alpha]_D^{20}+10.1°$;
(S)-4-[(2-Pyrrolidinyl)methyl]morpholine, boiling point $_{12\ mm\ Hg}$ 123° C.

EXAMPLE D

2-[(Diethylamino)methyl]piperidine and 3-[(Diethylamino)-hexahydro]-1H-azepine (a) 2-[(Diethylamino)methyl]piperidine, crude product A mixture of 2-(chloromethyl)-piperidine hydrochloride (418 g, 2.457 mol) (M. Rink and H. G. Liem, *Archiv der Pharmazie* 292, 165–169 [1959], diethylamine (2.487 liters, 24.17 mol), methanol (1.2 liters) and sodium iodide (4.13 g, 0.0276 mol) is refluxed until completely reacted (about 17 hours). The mixture is concentrated in vacuo, the residue is made alkaline with a solution of potassium hydroxide (150 g, 2.673 mol) in water (150 ml) and the resulting mixture is extracted four times, each time with diethyl ether (1 liter). The combined ether extracts are dried over sodium sulphate, freed from solvent and excess diethylamine and the residue is fractionally distilled under water jet vacuum. A colourless oil (218 g) is obtained, boiling point $_{20\ mm\ Hg}$ 92°–94° C., which, according to thin layer chromatography (ready-made silica gel plates 60° F. 254 Merck, eluant: dichloromethane/methanol/cyclohexane/conc. ammonia=68:15:15:2; detection: spraying with 1% aqueous KMnO$_4$ solution R$_F$ 0.47), is still contaminated with about 10% of an accompanying substance, R$_F$ 0.38. The fractions which go over at boiling point $_{20\ mm\ Hg}$ 94°–100° C . (55 g in all) are redistilled to yield a further 41.3 g of an oil of boiling point $_{20\ mm\ Hg}$ 95°–97° C. which contains a concentration of only about 3% of the accompanying substance. Total yield: 259.3 g.

The two fractions are combined and converted into the dihydrochloride in order to remove the unwanted 3-(diethylamino)-hexahydro-1H-azepine.

(b) 2-[(Diethylamino)methyl[piperidine dihydrochloride

A solution of hydrogen chloride gas (122.4 g, 3.357 mol) in 2-propanol (687 ml) is introduced with stirring, into a solution of the crude 2-[(diethylamino)methyl[-piperidine obtained n step (a) (259 g=1.521 mol) in 2-propanol (648 ml). The mixture heats up and turns dark in color. It is left to stand overnight at ambient temperature, then the precipitate is rapidly removed by suction filtration and washed eight times, each time with cold 2-propanol (15 ml). The salt, still damp with solvent, is then recrystallized from hot 2-propanol (400 ml), after which the crystals obtained are carefully freed from any adhering mother liquor by washing eight times, each time with 2-propanol (15 ml). The colorless product obtained is dried at 60° C. in a circulating air drier. The desired dihydrochloride (284 g) is obtained, m.p. 158°–160° C.

In TLC investigation (as in step a) no impurities are detected with an order of 200 γ; gas chromatography shows that the product still contains 0.1% of the accompanying substance 3-(diethylamino)-hexahydro-1H-azepine or the salt thereof.

(c) 3-(Diethylamino)-hexahydro-1H-azepine

The mother liquors of the preceding recrystallisations are combined and concentrated in vacuo. The residue is made alkaline and worked up in the usual way. The mixture of bases thus obtained is combined with the residues of the distillation described in (a). By carefully distilling several times with a 90 cm long column filled with ceramic fillers, a fraction with a boiling point $_{20\ mm\ Hg}$ 108°–109° C. is obtained. According to gas chromatography and spectroscopy, this fraction consists of at least 98.5% of 3-(diethylamino)-hexahydro-1H-azepine and, at most, 0.5% of 2-[(diethylamino)methyl]-piperidine.

EXAMPLE E

2-[(Diethylamino)methyl]-hexahydro-2H-azepin-2-one (a)

7-[(Diethylamino)methyl]-hexahydro-2H-azepin-2-one hydrochloride

While maintaining a reaction temperature of from −10° to −5° C., a solution azide (10.0 g, 0.154 mol) in as little water as possible is added dropwise to a solution of 2-[(diethylamino)methyl]-cyclohexanone (22.0 g, 0.1 mol) in concentrated hydrochloric acid (200 ml). After the cooling has been stopped, the mixture is stirred (48 minutes) at ambient temperature. After further cooling to −10° to −5° C., sodium azide, (5.0 g, 0.77 mol) is added in the same way as described above, after which the mixture is stirred for a further 24 hours at ambient temperature. Then, the reaction mixture is concentrated under water jet vacuum, the syrupy residue is taken up in 10 ml of water, mixed with substantially anhydrous sodium carbonate and stirred thoroughly with ethyl acetate (200 ml). After removal of the solvent the organic phase leaves an oily residue which can be converted into a hydrochloride by treatment with ethereal hydrogen chloride solution. M.p. 171° C. (ethyl acetate/methanol 3:1 v/v). Yield: 10.1 g.

(b) 2-[(Diethylamino)methyl]-hexahydro-1H-azepine

With external cooling, 7-[(diethylamino)methyl[-hexahydro-2H-azepin-2-one hydrochloride (10.0 g, 0.043 mol) is added in batches to a suspension of lithium aluminium hydride (1.9 g, 0.05 mol) in anhydrous tetrahydrofuran (500 ml) and the mixture is refluxed for 1 hour after the initially violent reaction has ended. The excess lithium aluminium hydride is decomposed by the dropwise addition of 20% sodium hydroxide solution. The tetrahydrofuran phase is separated off from the precipitate formed and concentrated in vacuo. The oily residue remaining is then distilled over caustic potash under water jet vacuum. A colorless oil (4.7 g) is obtained, boiling point $_{12\ mm\ Hg}$ 102°–105° C.

PREPARATION OF THE END PRODUCTS

EXAMPLE 1

3-Chloro-4-[[2-(Dimethylamino)methyl]-1-piperidinyl]-acetyl]-1-methyl-1,4,9,10-tetrahydropyrrolo[3,2-b][1,5]-benzodiazepin-10-one (a) 2,2,3-Trichloropropionitrile With stirring and illumination with a 300 watt daylight lamp, chlorine (426 g, 6.008 mol), dried over concentrated sulphuric acid, is introduced into of 3-chloropropionitrile (300 g, 3.351 mol) ($N_D^{20}$ 1.4383.). The reaction temperature is maintained at 70° to 80° C. After the reaction has ended the mixture is left to cool and then rinsed with nitrogen. The resulting product is fractionally distilled under water jet vacuum using a Vigreux column. The approximately 90% fraction (according to spectroscopy) with a boiling point $_{18\ mm\ Hg}$ 53°–60° C. ($N_D^{20}$ 1.4678) is used for the following reaction without any further purification.

Yield: 404.9 g.

(b) Mixture of diastereoisomers of 2-chloro-3-[[[(ethoxy)carbonyl]-methyl](methyl)amino]-2-propene nitrile A mixture of sarcosine ethyl ester (58.5 g, 0.499 mol), tetrahydrofuran (200 ml) and triethylamine (101.2 g, 1 mol) is added dropwise within 15 minutes to a solution of 2,2,3-trichloropropionitrile (79.0, 0.499 mol) in tetrahydrofuran (200 ml). Within 1 hour, the temperature of the mixture rises spontaneously to 30° C. To complete the reaction, the mixture is then refluxed for 3 hours. It is left to cool, stirred into diethyl ether (4 liters), filtered to remove the precipitated triethylamine hydrochloride and the etheral solution is concentrated. The residue is distilled under high vacuum to give a colorless oil (97.1 g), boiling point $_{0.3\ mm\ Hg}$ 120°–130° C. containing both isomers in a ratio of approximetely 1:1 according to $^1$H-NMR spectroscopy. An isomer, presumably the isomer of (E) configuration, crystallises out of this oil occasionally, mp. 57° C.

(c) Ethyl 3-amino-4-chloro-1-methyl-1H-pyrrole-2-carboxylate

Potassium ter.butoxide (0.5 g, 0.0044 mol) is placed in anhydrous toluene (300 ml). At ambient temperature, a solution of (E)-2-chloro-3-[[[(ethoxy)carbonyl]methyl]-(methyl)amino]-2-propene nitrile (58.0 g, 0.286 mol) (mp. 57° C.) in anhydrous toluene (200 ml) is added dropwise to the resulting suspension and the mixture is stirred for a further 30 minutes. It is then poured into ice water (1 liter), neutralized with acetic acid and then exhaustively extracted with dichloromethane. The combined extracts were dried over sodium sulphate and concentrated in vacuo. The residue remaining is recrystallized from diisopropyl ether/petroleum ether (1:1 v/v) and gives colorless crystals (50.0 g), m.p. 48° C.

(d) Ethyl 4-chloro-1-methyl-3-[(2-nitrophenyl)amino[-1H-pyrrole-2-carboxylate

With external cooling with ice, 80% sodium hydride (3.7 g) is added to a solution of ethyl 3-amino-4-chloro-1-methyl-1H-pyrrole-2-carboxylate (50.0 g, 0.247 mol) in dry dimethylformamide (300 ml). The mixture is allowed to come up to 10° C. and, while this temperature is maintained, a solution 2-fluoronitrobenzene (35.0 g, 0.248 mol) in anhydrous dimethylformamide (200 ml) is added dropwise thereto. Then, an 80% sodium hydride (3.7 g) dispersion is added to the resulting violet-colored solution and the mixture is stirred for 30 minutes at ambient temperature. The reaction mixture is then stirred into ice water (3 liters) and neutralized with acetic acid. The precipitate is suction filtered, washed thoroughly with water and recrystallized twice from methanol to give yellow crystals (54.0 g), m.p. 130°–131° C.

(e) Ethyl 3-[(2-aminophenyl)amino]-4-chloro-1-methyl-1H-pyrrole-2-carboxylate

A solution of ethyl 4-chloro-1-methyl-3-[(2-nitrophenyl) amino]-1H-pyrrole-2-carboxylate (35.6 g, 0.11 mol) in tetrahydrofuran (700 ml) is hydrogenated for 10 hours under a hydrogen pressure of 10 bar and at a temperature of 40° C. after the addition of Raney nickel (10 g). After a further Raney nickel (10 g) had been added, hydrogenation is continued for a further 13 hours under the same conditions, after which no further starting material is detected in the mixture by thin layer chromatography. The catalyst is filtered off, the filtrate is concentrated in vacuo and the syrupy residue is recrystallized once from tert.butyl methyl ether and once from methanol. The colorless crystals (27.5 g) melted at 104° to 105° C.

(f) 3-Chloro-1-methyl-1,4,9,10-tetrahydropyrrolo[3,2-b]-[1,5]benzodiazepin-10-one A mixture of ethyl 3-[(2-aminophenyl)amino]-4-chloro-1-methyl-1H-pyrrole-2-carboxylate (27.4 g, 0.0933 mol) and 85% phosphoric acid (90 ml) is heated to 110° C. under water jet vacuum for 2 hours with stirring. While still hot, the reaction mixture is then stirred into ice water (1 liter) and adjusted to pH 6 with aqueous ammonia solution. The solid obtained (23.0 g) melted at 172°–175° C. after recrystallisation from acetonitrile.

(g) 3-Chloro-4-(chloroacetyl)-1-methyl-1,4,9,10-tetrahydropyrrolo[3,2-b][1,5]benzodiazepin-10-one First, 3-chloro-1-methyl-1,4,9,10-tetrahydropyrrolo[3,2-b]-[1,5]benzodiazepin-10-one (1.7 g, 6.86 mmol), is refluxed for 1 hour in a mixture with acetonitrile (50 ml) and chloroacetyl chloride (4.0 ml, 52.9 mmol). The mixture is concentrated in vacuo, the residue is taken up in water (20 ml) and filtered and the solid residue is chromatographed using dichloromethane/cyclohexane/ethyl acetate (1:2:1 v/v) as eluant. A wine-red solid is isolated from the eluate, yielding colorless crystals (1.4 g) of mp. 284°–285° C. (D) after purification with tert.butyl methyl ether.

(h)
3-Chloro-4-[[2-[(dimethylamino)methyl]-1-piperidinyl]-acetyl]-1-methyl-1,4,9,10-tetrahydro-pyrrolo[3,2-d][1,5]benzodiazepin-10-one A mixture of 3-chloro-4-(chloroacetyl)-1-methyl-1,4,9,10-tetrahydropyrrolo-[3,2-b][1,5]benzodiazepin-10-one (8.0 g, 0.0247 mol), acetonitrile (100 m) and D,L-2-[(dimethylamino) methyl]piperidine (5.7 g, 0.04 mol) is refluxed for 3 hours.Then, further D,L-2-[(dimethylamino)methyl]piperidine (5.0 g. 0.035 mol) is added and the mixture is again refluxed for 2 hours. Activated charcoal (1.0 g) is added, the boiling hot mixture is filtered and then it is left to cool. After the filtrate has been left to stand for 2 hours at ambient temperature, colorless crystals (4.9 g) precipitate, mp. 226°–228° C. The mother liquor is diluted with dichloromethane (100 ml), washed successively with 1% aqueous sodium hydroxide solution, saturated with sodium hydrogen carbonate solution and water, then dried over sodium sulphate and concentrated. The residue melts after recrystallization from acetonitrile at 229°–230° C. According to thin layer chromatography (Polygram ® SIL G/UV$_{254}$; eluant: dichloromethane/cyclohexane/methanol/conc. ammonia 20.4:4.6:4.6:0.12; R$_F$ 0.1 to 0.3) the two fractions contained non-identical proportions of 2 diastereoisomers.

EXAMPLE 2

3-Chloro-4-[[[2-diethylamino)methyl]-1-piperidinyl]acetyl]-1-methyl-1,4,9,10-tetrahydropyrrolo[3,2-b][1,5]benzodi-azepin-10-one A mixture of 3-chloro-4-(chloroacetyl)-1-methyl-1,4,9,10-tetrahydropyrrolo[3,2-b]-[1,5]benzodiazepin-10-one (7.8 g, 0.024 mol), acetonitrile (200 ml), D,L-2-[(dimethylamino)methyl]piperidine (5.1 g, 0.03 mol) and sodium carbonate (3.3 g, 0.031 mol) are refluxed for 5 hours with stirring. Activated charcoal (1 g) is added, the mixture is filtered while hot and the evaporation residue of the filtrate is chromatographed on silica gel using dichloromethane/ethylacetate/cyclohexane/methanol/conc. ammonia (6.08:2:0.92:0.92:0.12) as eluant. After evaporation of the corresponding fractions, an eluate residue is obtained which is recrystallized from tert.butyl methyl ether and n-propanol. Colorless crystals (6.0 g) are obtained, m.p. 201° C. Thin layer chromatography under the conditions specified in Example 1h shows that the compound is present in the form of a mixture of 2 diastereoisomers in an approximate quantity ratio of 1:2. (R$_F$ 0.2 to 0.3).

EXAMPLE 3

4-[[2-[(Dimethylamino)methyl]-1-piperidinyl]acetyl]-1-methyl-1,4,9,10-tetrahydropyrrolo[3,2-b][1,5]benzodiazepin-10-one 3-Chloro-4-[[2-(dimethylamino)methyl]-1-piperidinyl]acetyl]-1-methyl-1,4,9,10-tetrahydropyrrolo[3,2-b][1,5]benzodiazepin-10-one (3.5 g, 8.14 mmol) were dissolved in hot ethanol (350 ml) and, after the addition of palladium on animal charcoal (3 g) (20%), hydrogenated for 20 hours under a hydrogen pressure of 50 bar and at a temperature of 40° C. The catalyst is removed by filtering, the filtrate is concentrated in vacuo, the crystalline hydrochloride is taken up in of water (20 ml), the resulting solution is made alkaline with sodium hydroxide and extracted exhaustively with dichloromethane. The combined extracts are dried over sodium sulphate and concentrated and the resulting residue is recrystallized once from ethylacetate and once from acetonitrile to give colorless crystals (1.7 g), mp. 163°–165° C.

EXAMPLE 4

4-[[2-[(Diethylamino)methyl]-1-piperidinyl]acetyl]-1-methyl-1,4,9,10-tetrahydropyrrolo[3,2-b][1,5]benzodiazepin-10-one The title compound is prepared analogously to Example 3 from 3-chloro-4-[[2-[(diethylamino)methyl]-1-piperidinyl]acetyl]-1-methyl-1,4,9,10-tetrhydropyrrolo[3,2-b][1,5]benzo-diazepin-10-one. Mp. 141°–144° C. (acetonitrile). Thin layer chromatography under the conditions specified in Example 1h indicates the presence of the compound in 2 diastereoisomeric forms (R$_F$ 0.2 to 0.3).

EXAMPLE 5

5,11-Dihydro-11-[[[2-dimethylamino)methyl]-1-piperidinyl]acetyl]-6H-pyrido[2,3-b][1,4]benzodiazepin-6-one The title compound is prepared analogously to Example 2 from 11-(chloroacetyl)-5,11-dihydro-6H-pyrido[2,3-b][1,4]benzodiazepin-6-one and D,L-2-[(dimethylamino)methyl]piperidine. Mp. 189°–190° C. (acetonitrile using activated charcoal).

Example 6

11-[3-[2-Diethylamino)methyl]-1-piperidinyl)-1-oxopropyl]-5,11-dihydro-6H-pyrido[2,3-b][1,4]benzodiazepin-6-one First, 11-(3-Chloro-1-oxopropyl)-5,11-dihydro-6H-pyrido[2,3-b][1,4]benzodiazepin-6-one (4.7 g, 0.0156 mol) is dissolved in acetonitrile (50 ml) and, after the addition of 2-[(diethylamino)-methyl]piperidine (3.4 g, 0.02 mol) and of triethylamine (2.8 ml, 0.03 mol), the mixture is refluxed (1 hour) with stirring. Then, 2-[(diethylamino)methyl]piperidine (1.0 g, 0.059 mol) is added and the mixture is heated to reflux temperature for a further 4 hours. The cooled mixture is concentrated and the residue is distributed between water and dichloromethane. The dichloromethane phase is dried over sodium sulphate, concentrated and purified by column chromatography on silica gel using acetonitrile/dichloromethane/ethyl acetate/cyclohexane/methanol/conc. ammonia (6:3.5:1.5:0.46:0.46:0.06) as eluant. After recrystallisation from acetonitrile using activated charcoal, colorless crystals (3.8 g) are obtained, mp. 160°–162° C.

EXAMPLE 7

5,11-Dihydro-11-[[2-[2-dimethylamino)ethyl]-1-piperidinyl]acetyl]-6H-pyrido[2,3-b][1,4]benzodiazepin-6-one The title compound is prepared analogously to Example 6 from 11-(chloroacetyl)-5,11-dihydro-6H-pyrido[2,3-b][1,4]benzodiazepin-6-one and 2-[2-[(dimethylamino)ethyl]]piperidine in the presence of triethylamine and gives colorless crystals, mp. 181°–183° C. (acetonitrile).

The following are obtained analogously:

5,11-Dihydro-11-[[2-[(ethylmethylamino)methyl]-1-piperidinyl]acetyl]-6H-pyrido[2,3-b][1,4]benzodiazepin-6-one, Mp. 200°–202° C. (acetonitrile);

11-[[2-[(Diethylamino)methyl]-hexahydro-1H-azepin-1-yl]-acetyl]-5,11-dihydro-6H-pyrido[2,3-b][1,4]benzodiazepin-6-one;

5,10-Dihydro-5-[[2-[(ethylmethylamino)methyl]-1-piperidinyl]acetyl]-11H-dibenzo[b,e][1,4]diazepin-11-one, Mp. 154°–156° C. (acetonitrile/ethyl acetate 1:1 v/v);

5,11-Dihydro-11-[[2-[[(2-hydroxyethyl)(methyl)amino]-methyl]-1-piperidinyl]acetyl]-6H-pyrido[2,3-b][1,4]benzodiazepin-6-one, Mp. 176°–177° C. (acetonitrile);

5,10-Dihydro-5-[[2-[[(2-hydroxyethyl)(methyl)amino]-methyl-1-piperidinyl]acetyl]-11H-dibenzo[b,e][1,4-]diazepin-11-one, Mp. 133°–134° C. (ethyl acetate/activated charcoal);

5,11-Dihydro-11-[[2-[[(methyl)(2-methylpropyl)amino]-methyl]-1-piperidinyl]acetyl]-6H-pyrido[2,3-b][1,4]benzodiazepin-6-one;

5,10-Dihydro-5-[[2-(methyl)(2-methylpropyl)amino]-methyl]-1-piperidinyl]acetyl]-11H-dibenzo[b,e][1,4-]diazepin-11-one;

5,11-Dihydro-11-[[2-[[methylpropylamino]methyl]-1-piperidinyl]acetyl]-6H-pyrido[2,3-b][1,4]benzodiazepin-6-one;

5,10-Dihydro-5-[[2-[[methylpropyl]amino]methyl]-1-piperidinyl]acetyl]-11H-dibenzo[b,e][1,4]diazepin-11-one;

11-[[2-[[Butylmethylamino]methyl]-1-piperidinyl]acetyl]-5, 11-dihydro-6H-pyrido[2,3-b][1,4]benzodiazepin-6-one, Mp. 155°–156° C. (acetonitrile);

5-[[2-[[Butylmethylamino]methyl]-1-piperidinyl]acetyl]-5,10-dihydro-11H-dibenzo[b,e][1,4]diazepin-11-one, Mp. 135°–136° C. (ethyl acetate/activated charcoal);

5,11-Dihydro-11-[[3-[(dimethylamino)methyl]-4-morpholinyl]acetyl]-6H-pyrido[2,3-b][1,4]benzodiazepin-6-one;

5,10-Dihydro-5-[[3-(dimethylamino)methyl]-4-morpholinyl]-acetyl]-11H-dibenzo[b,e][1,4]diazepin-11-one;

5-[[2-[(Dimethylamino)methyl]-hexahydro-1H-azepin-1-yl]acetyl]-5,10-dihydro-11H-dibenzo[b,e][1,4]diazepin-11-one;

5,11-Dihydro-11-[[2-[(1-pyrrolidinyl)methyl]-hexahydro-1H-azepin-1-yl]acetyl]-6H-pyrido[2,3-b][1,4]benzodiazepin-6-one;

5,10-Dihydro-5-[[2-[(1-pyrrolidinyl)methyl]-hexahydro-1H-azepin-1-yl]acetyl]-11H-dibenzo[b,e][1,4-]diazepin-11-one;

5,11-Dihydro-11-[[2-[(4-methyl-1-piperazinyl)methyl]-hexahydro-1H-azepin-1-yl]acetyl]-6H-pyrido[2,3-b][1,4]benzodiazepin-6-one;

5,10-Dihydro-5-[[2-[(4-methyl-1-piperazinyl)methyl]-hexahydro-1H-azepin-1-yl]acetyl]-11H-dibenzo[b,e][1,4]diazepin-11-one;

EXAMPLE 8

11-[[2-[2-(Diethylamino)ethyl]-1-piperidinyl]acetyl]-5,11-dihydro-6H-pyrido[2,3-b][1,4]benzodiazepin-6-one;

The title compound is prepared analogously to Example 2 from 11-(chloroacetyl)-5,11-dihydro-6H-pyrido[2,3-b][1,4]benzodiazepin-6-one and 2-[2-(diethylamino)ethyl]-piperidine to give colorless crystals, mp. 137°–139° C. (diisopropyl ether).

EXAMPLE 9

5,11-Dihydro-11-[[2-[(1-pyrrolidinyl)methyl-1-piperidinyl]-acetyl]-6H-pyrido[2,3-b][1,4]benzodiazepin-6-one A mixture of 11-(chloroacetyl)-5,11-dihydro-6H-pyrido[2,3-b][1,4]benzodiazepin-6-one (8.6 g, 0.0299 mol), sodium carbonate (3.9 g, 0.0283 mol), ethanol (250 ml) and 2-[(1-pyrrolidinyl)methyl]piperidine (5.9 g, 0.035 mol) is refluxed for 9 hours. It is then filtered and the filtrate is concentrated in vacuo. The residue crystallizing out is recrystallized once from isopropanol using animal charcoal and once from a large quantity of acetonitrile to give colorless crystals (3.2 g), mp. 230°–231° C.

EXAMPLE 10

5,11-Dihydro-11-[[2-[(4-morpholinyl)methyl]-1-piperidinyl]-acetyl]-6H-pyrido[2,3-b][1,4]benzodiazepin-6-one The title compound is prepared analogously to Example 2 from 11-(chloroacetyl)-5,11-dihydro-6H-pyrido[2,3-b][1,4]benzodiazepin-6-one and 2-[(4-morpholinyl)methyl]piperidine to give colorless crystals, mp. 203°–205° C. (acetonitrile using activated charcoal).

EXAMPLE 11

11-[[2-[[(Cyclohexyl)(methyl)]amino]methyl]-1-piperidinyl]-acetyl]-5,11-dihydro-6H-pyrido[2,3-b][1,4]benzodiazepin-6-one The title compound is prepared analogously to Example 2 from 11-(chloroacetyl)-5,11-dihydro-6H-pyrido[2,3-b][1,4]benzodiazepin-6-one and 2-[[(cyclohexyl)(methyl)amino]methyl]-piperidine to give colorless crystals, mp. 175°–177° C. (acetonitrile using activated charcoal).

EXAMPLE 12

5,11-Dihydro-11-[[2-[1-piperidinyl)methyl]-1-piperidinyl]acetyl]-6H-pyrido[2,3-b][1,4]benzodiazepin-6-one The title compound is prepared analogously to Example 2 from 11-(chloroacetyl)-5,11-dihydro-6H-pyrido[2,3-b][1,4]benzodiazepin-6-one and 2-[(1-piperidinyl)methyl]piperidine to give colorless crystals, mp. 212°–214° C. (ethanol).

EXAMPLE 13

5,11-Dihydro-11-[[2-[(4-methyl-1-piperazinyl)-methyl]-1-piperidinyl]acetyl]-6H-pyrido[2,3-b][1,4]benzodiazepin-6-one The title compound is prepared analogously to Example 2 from 11-(chloroacetyl)-5,11-dihydro-6H-pyrido[1,3-b][1,4]benzodiazepin-6-one and 2-[(4-methyl-1-piperazinyl)methyl]-piperidine to give colorless crystals, mp. 203°–205° C. (after recrystallization from isopropanol and acetonitrile). Under the conditions (HPLC, TLC) which results in separation of the diastereoisomers in Example 24, no isomers could be detected.

EXAMPLE 14 trans-5,11-Dihydro-11-[[2-[[(4-hydroxycyclohexyl)-(methyl)-amino]methyl]-1-piperidinyl]acetyl]-6H-pyrido[2,3-b][1,4]-benzodiazepin-6-one The title compound is prepared analogously to Example 2 from 11-(chloroacetyl)-5,11-dihydro-6H-pyrido[2,3-b][1,4]benzodiazepin-6-one and trans-2-[[(4-hydroxycyclohexyl)(methyl)-amino]methyl]piperidine to give colorless crystals, mp. 183°–184.5° C. (acetonitrile).

EXAMPLE 15

5-[[2-[(Diethylamino)methyl]-1-piperidinyl]acetyl]-5,10-dihydro-11H-dibenzo[b,e][1,4]-diazepin-11-one A mixture of 4-(chloroacetyl)-5,10-dihydro-11H-dibenzo[b,e][1,4]diazepin-11-one (5.1 g, 0.0178 mol), 2-[(diethylamino)methyl]piperidine (3.2 g, 0.0188 mol) and dimethylformamide (20 ml) is heated to 80° C. for 3 hours. It is left to cool, stirred into ice water (100 ml) and saturated with solid soda. It is then extracted exhaustively with ethyl acetate. The combined ethyl acetate extracts are washed once with a little water, dried over sodium sulphate and concentrated in vacuo. The remaining residue is crystallized from ethanol to give colorless crystals (0.8 g), mp. 171°–172° C.

EXAMPLE 16

5-[3-[2-[(Diethylamino)methyl]-1-piperidinyl]-1-oxopropyl]-5,10-Dihydro-11H-dibenzo[b,e][1,4]diazepin-11-one The title compound is prepared analogously to Example 1h from 5,10-dihydro-5-(1-oxopropen-1-yl)-11H-dibenzo[b,e][1,4]diazepin-11-one and 2-[(diethylamino)-methyl]piperdine to give colorless crystals mp. 125°–127° C. (acetonitrile).

EXAMPLE 17

5,10-Dihydro-5-[[2-[(dimethylamino)methyl]-1-piperidinyl]-acetyl]-11H-dibenzo[b,e][1,4]diazepin-11-one The title compound is prepared analogously to Example 2 from 5-(chloroacetyl)-5,10-dihydro-11H-dibenzo[b,e][1,4]diazepin-11-one and 2-[(dimethylamino)methyl]piperidine to give colorless crystals, mp. 123°–125° C. (diisopropyl ether).

EXAMPLE 18

5,10-Dihydro-5-[[2-[2-(dimethylamino)ethyl]-1-piperidinyl]-acetyl]-11H-dibenzo[b,e][1,4]diazepin-11-one The title compound is prepared analogously to Example 2 from 5-(chloroacetyl)-5,10-dihydro-11H-dibenzo[b,e][1,4]diazepin-11-one and 2-[2-(dimethylamino)ethyl]piperidine to give colorless crystals, mp. 155°–157° C. (acetonitrile).

EXAMPLE 19

5-[[2-[2-(Diethylamino)ethyl]-1-piperidinyl]-acetyl]-5,10-dihydro-11H-dibenzo[b,e][1,4]diazepin-11-one The title compound is prepared analogously to Example 2 from 5-(chloroacetyl)-5,10-dihydro-11H-dibenzo[b,e][1,4]diazepin-11-one and 2-[2-(diethylamino)ethyl]piperidine to give colorless crystals, mp 97°–98° C. (diisopropyl ether).

EXAMPLE 20

5,10-Dihydro-5-[[2-[(1-pyrrolidinyl)methyl]-1-piperidinyl]-acetyl]-11H-dibenzo[b,e][1,4]diazepin-11-one The title compound is prepared analogously to Example 2 from 5-(chloroacetyl)-5,10-dihydro-11H-dibenzo[b,e][1,4]diazepin-11-one and 2-[(1-pyrrolidinyl)methyl]piperidine to give colorless crystals, mp. 199°–201° C. (isopropanol/activated charcoal).

EXAMPLE 21

5,10-Dihydro-5-[[2-[(4-morpholinyl)methyl]-1-piperidinyl]-acetyl]-11H-dibenzo[b,e][1,4]diazepin-11-one The title compound is prepared analogously to Example 2 from 5-(chloroacetyl)-5,10-dihydro-11H-dibenzo[b,e][1,4]diazepin-11-one and 2-[(4-morpholinyl)methyl]piperidine to give colorless crystals, mp. 194°–195° C. (after recrystallisation from diisopropyl ether and acetonitrile using activated charcoal).

EXAMPLE 22

5-[[2-[[(Cyclohexyl)(methyl)amino]methyl]-1-piperidinyl]-acetyl]-5,10-dihydro-11H-dibenzo[b,e][1,4-]diazepin-11-one The title compound is prepared analogously to Example 2 from 5-(chloroacetyl)-5,10-dihydro-11H-dibenzo[b,e][1,4]diazepin-11-one and 2-[[cyclohexyl)(methyl)amino]methyl]piperidine to give colorless crystals, mp. 146°–148° C. (acetonitrile activated charcoal).

EXAMPLE 23

5,10-Dihydro-5-[[2-[(1-piperidinyl)methyl]-1-piperidinyl]acetyl]-11H-dibenzo[b,e][1,4]diazepin-11-one The title compound is prepared analogously to Example 2 from 5-(chloroacetyl)-5,10-dihydro-11H-dibenzo[b,e][1,4]diazepin-11-one and 2-[(1-piperidinyl)methyl]piperidine to give colorless crystals, mp. 220°–221° C. (acetonitrile).

EXAMPLE 24

5,10-Dihydro-5-[[2-[(4-methyl-1-piperazinyl)methyl]-1-piperidinyl]-acetyl]-11H-dibenzo[b,e][1,4]diazepin-11-one The title compound is prepared analogously to Example 2 from 5-(chloroacetyl)-5,10-dihydro-11H-dibenzo[b,e][1,4]diazepin-11-one and D,L-2-[(4-methyl-1-piperazinyl)methyl]-piperidine to give colorless crystals, mp. 200°–202° C. (acetonitrile/activated charcoal). According to thin layer chromatography (Polygram ® SIL G/UV$_{254}$; eluant: dichloromethane/ethyl acetate/-cyclohexane/methanol/conc. ammonia 3.5:1.5:0.46:0.46:0.06; R$_F$ approx. 0.25) it is a mixture of isomers in a quantity ratio of approximately 1:1. Preparative separation is carried out by the following method:

(a) By liquid chromatography (HPLC):

Apparatus: liquid chromatography series III B, Perkin-Elmer:
Detector: LC 75 spectrophotometer and LC 75 autocontrol; Perkin-Elmer;
Injector: Rheodyn inlet valve 7125 with 250 μl sample slide;
Recorder: Type 561, Perkin-Elmer;
Integrator: System I autocontrol, Spectra Physics;
Column: Silica A 25×0.25 cm (polar);
Mobile Phase: Methylene chloride/cyclohexane/methanol/conc. ammonia (200:210:40:0.5 v/v);
Temperature: 21° C;
Running: Isocratic;
Flow 0.8 ml/min;
Detection: 270 nm;
Sensitivity: 512 $A_{1\ cm}$;
Integrator: Recorder attenuator =1;
Paper feed: 5 mm/min.

In each case, a solution (100 μl) of the diastereoisomer mixture (15.2 mg) is injected into the mobile phase (1 ml) and thus placing the substance (1.5 mg) on the column.

Results: Isomer I, t 11.1 minutes, 46.2% of the mixture; Isomer II, t 14.7 minutes, 53.8% of the mixture.

Isomer I reverts into the original mixture at ambient temperature and in the above mentioned mobile phase at $t_{\frac{1}{2}}<9$ days; isomer II reverts into the original mixture at $t_{\frac{1}{2}}<6.5$ days.

(b) By liquid chromatography on a Jobin-Yvon chromatospac Prep using Li Chroprep Si 60, 25–40 μm (Merck-Darmstadt, Art. 9390) under a pressure of 10 bar.

Isomer I; Mp. 196°–198° C.; uniform according to thin layer chromatography (Polygram® SIL G/UV$_{254}$; eluant: dichloromethane/methanol/cyclohexane/conc. ammonia =180:40:40.1; $R_F$ 0.4). IR, UV, MS identical with that of Isomer II.

$^1$H-NMR (CDCl$_3$, 400 HMz): 9.6 and 10.21 (1H, exchangeable H), 7.97 (1H, broad, ar.H) 7.60 (1H-m, ar.H); 7.1–7.55 (6H-m; ar.H); 4.0 (ca. 0.5 H-d; J=17 Hz); 3.85 (ca. 0.5 H-d; J=17 Hz); 3.55 (ca. 0.5 H-d; J=17 Jz); 3.23 (ca. 0.5 H-d; J=17 Hz); 0.9–2.8 (22H-m; aliph.H); the signals at 4.0; 3.85; 3.55 and 3.23 indicate the presence of rotational isomers.

Isomer II: Mp. 205° C., uniform according to TLC R$_F$ 0.35). $^1$H-NMR(CDCl$_3$, 400 MHz); 9.94 and 9.42 (1H, exchangeable H); 7.99 (1H, broad, ar.H); 7.58 (1H, broadened, ar.H); 7.1–7.52 (6H-m; ar.H); 4.02 (1H-t; J=17 Hz); 3.39 (ca. 0.5H-d; J=17 Hz); 3.17 (ca. 0.5H-d; J=17 Hz); 0.9–2.85 (22H-m; aliph.H); the signals at 4.02; 3.39 and 3.17 indicate the presence of two rotational isomers.

Isomers I and II are completely stable in crystalline form and at temperature below the melting point.

EXAMPLE 25 trans-5,10-Dihydro-5-[[2-[[(4-hydroxycyclohexyl)(methyl)-amino]methyl]-1-piperidinyl]acetyl]-11H-dibenzo[b,e][1,4]diazepin-11-one The title compound is prepared analogously to Example 2 from 5-(chloroacetyl-5,10-dihydro-11H-dibenzo[b,e][1,4]diazepin-11-one and trans-2-[[(4-hydroxycyclohexyl)(methyl)amino]-methyl]piperidine to give colorless crystals, Mp. 161°–162° C. (acetonitrile).

EXAMPLE 26

4,9-Dihydro-4-[[2-[(dimethylamino)methyl]-1-piperidinyl]-acetyl]-10H-thieno[3,4-b][1,5]benzodiazepin-10-one The title compound is prepared analogously to Example 2 from 4-(chloroacetyl)-4,9-dihydro-10H-thieno[3,4-b][1,5]benzodiazepin-10-one and 2-[(dimethylamino)methyl]piperidine to give colorless crystals, Mp. 208°–209° C. (acetonitrile/activated charcoal).

EXAMPLE 27

4-[[2-[(Diethylamino)methyl]-1-piperidinyl]acetyl]-4,9-dihydro-10H-thieno[3,4-b][1,5]benzodiazepin-10-one The title compound is prepared analogously to Example 2 from 4-(chloroacetyl)-4,9-dihydro-10H-thieno[3,4-b][1,5]benzodiazepin-10-one and 2-[(dimethylamino)methyl]piperidine to give colorless crystals, Mp. 163°–164° C. (acetonitrile).

EXAMPLE 28

4,9-Dihydro-4-[[2-[(1-piperidinyl)methyl]-1-piperidinyl]-acetyl]-10H-thieno[3,4-b][1,5]benzodiazepin-10-one The title compound is prepared analogously to Example 2 from 4-(chloroacetyl)-4,9-dihydro-10H-thieno[3,4-b][1,5]benzodiazepin-10-one and 2-[(dimethylamino)methyl]piperidine to give colorless crystals, Mp. 190°–195° C. (acetonitrile).

EXAMPLE 29

4,9-Dihydro-4-[[2-[(1-pyrrolidinyl)methyl]-1-piperidinyl]-acetyl]-10H-thieno[3,4-b][1,5]benzodiazepin-10-one The title compound is prepared analogously to Example 2 from 4-(chloroacetyl)-4,9-dihydro-10H-thieno[3,4-b][1,5]benzodiazepin-10-one and 2-[(1-pyrrolidinyl)methyl]piperidine to give colorless crystals, Mp. 205°–207° C. (acetonitrile/activated charcoal).

EXAMPLE 30

4,9-Dihydro-4-[[2-[(1-morpholinyl)methyl]-1-piperidinyl]-acetyl]-10H-thieno[3,4-b][1,5]benzodiazepin-10-one The title compound is prepared analogously to Example 2 from 4-(chloroacetyl)-4,9-dihydro-10H-thieno[3,4-b][1,5]benzodiazepin-10-one and 2-[(4-morpholinyl)methyl]piperidine to give colorless crystals, Mp. 193°–194° C. (acetonitrile/activated charcoal).

EXAMPLE 31

4-[[2-[(Diethylamino)methyl]-1-piperidinyl]acetyl]-1,3-dimethyl-1,4,9,10-tetrahydropyrrolo[3,2-b][1,5]benzodiazepin-10-one A mixture of 4-(chloroacetyl)-1,3-dimethyl-1,4,9,10-tetrahydropyrrolo[3,2-b][1,5]-benzodiazepin-10-one (2.0 g, 0.0066 mol), dimethylformamide (30 ml), triethylamine (1 ml, 0.0071 mol) and 2-[(diethylamino)methyl]piperidine (1.7 g, 0.01 mol) is heated to 30°–40° C. for two hours with stirring. The solvent is distilled off under water jet vacuum, the residue taken up in water (10 ml), made alkline with potassium carbonate and extracted exhaustively with dichloromethane. The combined methylene chloride extracts are dried over sodium sulfate and concentrated. The crude product thus obtained is purified by chromatography on silica gel using dichloromethane/methanol (9:1 v/v). After recrystallization from ethyl acetate/methanol (95:5) the desired compound (1.4 g) is obtained in the form of colorless crystals, Mp. 176°–178° C.

EXAMPLE 32

11-[[2-[(Diethylamino)methyl]-1-piperidinyl]acetyl]-5,11-Dihydro-6H-pyrido[2,3-b][1,4]benzodiazepin-6-one First, 11-(chloroacetyl)-5,11-dihydro-6H-pyrido-[2,3-b][1,4]benzodiazepin-6-one (5.0 g, 0.0174 mol) is dissolved in anhydrous dioxan (100 ml) and refluxed for 2 hours after the addition of 2-[(diethylamino)methyl]-piperidine (6.0 g, 0.035 mol).

The mixture is concentrated, and then the residue is recrystallized once from ethanol and once from methanol with the addition of a large quantity of activated charcoal. Colorless crystals are obtained (1.5 g), Mp. 225°–225° C.

EXAMPLE 33

11-[[2-[(Diethylamino)methyl]-1-piperidinyl]acetyl]-5,11,-dihydro-6H-pyrido[2,3-b][1,4]benzodiazepin-6-one The title compound is prepared analogously to Example 2 from 11-(chloroacetyl)-5,11-dihydro-6H-pyrido[2,3-b][1,4]benzodiazepin-6-one and 2-[(diethylamino)methyl]piperidine to give colorless crystals, Mp. 225°–225.5° C. (n-propanol).

EXAMPLE 34

11-[[2-[(Diethylamino)methyl]-1-piperidinyl]acetyl]-5,11-dihydro-6H-pyrido[2,3-b][1,4]benzodiazepin-6-one A mixture of 11-(chloroacetyl)-5,11-dihydro-6H-pyrido-[2,3-b][1,4]benzodiazepin-6-one (97.6 g, 0.339 mol), 2-[(diethylamino)methyl]piperidine (64.0 g, 0.376 mol), sodium carbonate (36.0 g, 0.34 mol) and n-propanol (1.7 liters) is refluxed for 5 hours. The reaction mixture is filtered while hot then left to stand for 12 hours at ambient temperature, after which the desired product is found to have precipitated in crystalline form. The substance is suction filtered, washed 3 times, each time with n-propanol (100 ml), and dried in a vacuum drying chamber. Colorless crystals (119.5 g) are obtained, Mp. 226°–229° C.

The following salts were prepared by conventional methods:

Methanesulphonate: $C_{24}H_{31}N_5O_2 \cdot CH_3SO_3H$, Mp. 220°–222° C. (Ethanol);
Fumarate: $C_{24}H_{31}N_5O_2 \cdot C_4H_4O_4$, Mp. 192°–194° C. (isopropanol);
Maleate: $C_{24}H_{31}N_5O_2 \cdot C_4H_4O_4$, Mp. 175°–177° C. (isopropanol);
Dichlorochloride-dihydrate: $C_{24}H_{31}N_5O_2 \cdot 2HCl \cdot 2H_2O$, Mp. 229°–230° C. (D) (isopropanol/methanol 1:1)
Dihydrobromide: $C_{24}H_{31}N_5O_2 \cdot 2HBr$, Mp. 249°–250° C. (ethanol)

The base could not be separated into diastereoisomers using method (a) given in Example 24.

EXAMPLE 35

11-[[3-[(Diethylamino)methyl]-1-piperidinyl]acetyl]-5,11-dihydro-6H-pyrido[2,3-b][1,4]benzodiazepin-6-one A solution of 3-[(diethylamino)-methyl]piperidine (4.6 g, 0.027 mol) in dry dimethylformamide (10 ml) is added dropwise over 2 hours to a suspension of 11-chloroacetyl-5,11-dihydro-6H-pyrido[2,3-b][1,4]benzodiazepin-6-one (5.2 g, 0.0181 mol) in anhydrous dimethylformamide (25 ml), then the resulting mixture is stirred for a further 6 hours at ambient temperature and left to stand overnight. The mixture is stirred into ice (200 g), made alkaline with postassium carbonate and extracted exhaustively with dichloromethane. The combined dichloromethane extracts are washed once with water (20 ml), dried over magnesium sulphate and concentrated by evaporation in vacuo. After recrystallization from ethyl acetate, colorless crystals (4.5 g) are obtained, mp. 199°–200° C.

EXAMPLE 36

(S)-11-[[2-[(Diethylamino)methyl]-1-pyrrolidinyl]-acetyl]-5,11-dihydro-6H-pyrido[2,3-b][1,4]benzodiazepin-6-one The title compound is prepared analogously to Example 31 from 11-(chloroacetyl)-5,11-dihydro-6H-pyrido[2,3-b][1,4]benzodiazepin-6-one and (S)-(+)-2-[(diethylamino)methyl]pyrrolidine to give colorless crystals, mp. 192°–193° C. (ethyl acetate/methanol 99:1 v/v); $[\alpha]_D^{20} = 29.4°$ (ethanol).

EXAMPLE 37

5,11-Dihydro-11-[[(3-dimethylamino)-1-piperidinyl]acetyl]-6H-pyrido[2,3-b][1,4]benzodiazepin-6-one The title compound is prepared analogously to Example 35 from 11-(chloroacetyl)-5,11-dihydro-6H-pyrido[2,3-b][1,4]benzodiazepin-6-one and 3-(dimethylamino)piperidine to give colorless crystals, mp. 211°–212° C. (diisopropyl ether).

EXAMPLE 38

(S)-5,11-Dihydro-11-[[2-[(1-pyrrolidinyl)methyl]-1-pyrrolidinyl]acetyl]-6H-pyrido[2,3-b][1,4]benzodiazepin-6-one The title compound is prepared analogously to Example 31 from 11-(chloroacetyl)-5,11-dihydro-6H-pyrido[2,3-b][1,4]benzodiazepin-6-one and (S)-(+)-2-[(1-pyrrolidinyl)methyl]pyrrolidine to give colorless crystals, mp. 192°–193° C. (ethyl acetate). $[\alpha]_D^{20} = -18.1°$ (ethanol).

Example 39

5,11-Dihydro-5-[[3-(dimethylamino)-1-piperidinyl]acetyl]-1-11H-dibenzo[b,e][1,4]diazepin-11-one The title compound is prepared analogously to Example 35 from 5-(chloroacetyl)-5,10-dihydro-11H-dibenzo[b,e][1,4]diazepin-11-one and 3-(dimethylamino)piperidine to give colorless crystals, mp. 199°–200° C. (diisopropyl ether).

EXAMPLE 40

(S)-5,10-Dihydro-5-[[2-[(1-pyrrolidinyl)methyl]-1-pyrrolidinyl]-acetyl]-11H-dibenzo[b,e][1,4]diazepin-11-one The title compound is prepared analogously to Example 31 from 5-(chloroacetyl)-5,10-dihydro-11H-dibenzo[b,e][1,4]diazepin-11-one and (S)-(+)-2-[(1-pyrrolidinyl)methyl]pyrrolidine to give colorless crystals, mp. 142°–144° C. (ethyl acetate/methanol 99:1 v/v); $[\alpha]_D^{20} = -18.5°$ (ethanol).

EXAMPLE 41

5-[[3-[(Diethylamino)methyl]-1-piperidinyl]acetyl]-5,10-dihydro-11H-dibenzo[b,e][1,4]diazepin-11-one dihydrochloride dihydrate The title compound is prepared analogously to Example 35 from 5-(chloroacetyl)-5,10-dihydro-11H-dibenzo[b,e][1,4]diazepin-11-one and 3-[(diethylamino)methyl]piperidine to give colorless crystals, mp. 140° C. (isopropanol/ethyl acetate).

EXAMPLE 42

(S)-5-[[2-[(Diethylamino)methyl]-1-pyrrolidinyl]acetyl]-5,10-dihydro-11H-dibenzo[b,e][1,4]diazepin-11-one The title compound is prepared analogously to Example 31 from 5-(chloroacetyl)-5,10-dihydro-11H-dibenzo[b,e][1,4]diazepin-11-one and (S)-(+)-2-[(diethylamino)methyl]pyrrolidine to give a colorless highly viscous oil, $[\alpha]_D^{20} = -10.5°$ (ethanol).

Elemental Analysis for $C_{24}H_{30}N_4O_2$: Calculated: C, 70.91; H, 7.44; N, 13.78. Found: C, 70.55; H, 7.32; N, 13.48.

IR($CH_2Cl_2$):NH 3370/cm; CO 1640–1700/cm (broad)

| UV (ethanol): | max (neutral): | 270 nm (E = 0.075) (shoulder) |
|---|---|---|
| | max (basic): | 252 nm (E = 0.11) (shoulder) |
| | | 290 nm (E = 0.83) (shoulder) |

(c=50 mg/l; layer thickness: 2 mm)
$^1$H-NMR (CDCl$_3$/CD$_3$OD; 400 MHz): 7.92 (1H-d; ar.H); 7.58–7.66 (1H-m; ar.H); 7.1–7.54 (6H-m;ar.H); 4.05–4.21(t); 3.8–3.9(d); 3.7–3.8(d); 3.24–3.33(d); 3.2–1.3(m); (altogether 15 aliph.H); 0.85–1.05 (6H-,;aliph.H).

EXAMPLE 43

(S)-5,10-Dihydro-5-[[2-[(4-methyl-1-piperazinyl)methyl]-1-pyrrolidinyl]-acetyl]-11H-dibenzo[b,e][1,4-]diazepin-11-one The title compound is prepared analogously to Example 31 from 5-(chloroacetyl)-5,10-dihydro-11H-dibenzo[b,e][1,4]diazepin-11-one and (S)-(+)-2-[(4-methyl-1-piperazinyl)methyl]pyrrolidine to give colorless crystals, mp. 168°–170° C. (ethyl acetate). $[\alpha]_D^{20} = -18.9°$ C. (ethanol). R$_F$ 0.33 (Merck ready-made TLC plates, silica gel 60 F-254; eluant: dichloromethane/methanol/cyclohexane/conc. ammonia [120:24:30:2]). A second isomer (R$_F$ 0.30) can be detected in the mother liquors by thin layer chromatography.

EXAMPLE 44

(S)-5,11-Dihydro-11-[[2-[(4-methyl-1-piperazinyl)methyl]-1-pyrrolidinyl]-acetyl]-6H-pyrido[2,3-b][1,4]benzodiazepin-6-one The title compound is prepared analogously to Example 31 from 11-(chloroacetyl)-5,11-dihydro-6H-pyrido[2,3-b][1,4]benzodiazepin-6-one and (S)-(+)-2-[(4-methyl-1-piperazinyl) methyl]pyrrolidine to give colorless crystals, mp. 182°–185° C. (D) (from ethyl acetate/methanol 99:1 v/v); $[\alpha]_D^{20} = -11.2°$ (ethanol).

EXAMPLE 45

5,11-Dihydro-11-[[4-(dimethylamino)-1-piperidinyl]acetyl]-6H-pyrido[2,3-b][1,4]benzodiazepin-6-one-hydrochloride First, 11-(chloroacetyl)-5,11-dihydro-6H-pyrido[2,3-b][1,4]benzodiazepin-6-one (7.0 g, 0.0243 mol) is suspended in anhydrous dioxan (150 ml) and refluxed for 3 hours after the addition of 4-(dimethylamino)piperidine hydrochloride (4.9 g, 0.0298 mol) and triethylamine (10.0 g, 0.099 mol). Then the mixture is concentrated in vacuo. The residue is made alkaline with sodium hydroxide and extracted exhaustively with dichloromethane. The combined dichloromethane extracts are dried over sodium sulphate and concentrated. The highly viscous residue is taken up in dioxan, clarified with activated charcoal and mixed with ethereal hydrochloric acid solution. The colorless crystals (2.0 g) obtained melted 258° C. after recrystallization from methanol.

EXAMPLE 46

11-[[2-[(Diethylamino)methyl]-1-piperidinyl]acetyl]-5,11-Dihydro-6H-pyrido[2,3-b][1,4]benzodiazepin-6-one A mixture of 2-[(diethylamino) methyl]-1-piperidinoacetic acid (14.43 g. 0.0632 mol) and a 75% sodium hydride dispersion (2.0 g) in paraffin oil is heated in dimethylformamide (160 ml) at 50° to 80° C. until the development of hydrogen has ceased. The resulting sodium salt of the above-mentioned acid is combined with 5,11-dihydro-6H-pyrido[2,3-b][1,4]benzodiazepin-6-one (13.2 g, 0.0625 mol). Then, phosphorous oxychloride (9.9 g, 0.0646 mol) is added dropwise over 10 minutes at −10° C. The resulting mixture is stirred for 4 hours at −10° C., for 4 hours at 0° C. and for 20 hours at ambient temperature. The mixture is stirred into ice (300 g), adjusted to pH 9 with sodium hydroxide solution and extracted exhaustively with dichloromethane. The combined organic phases are washed once with a little ice water, dried over sodium sulphate and concentrated. The residue is recrystallized from n-propanol using active charcoal to give colorless crystals (4.1 g), mp. 226°–229° C., which are shown by thin layer chromatography, mixed melting point, IR, UV and $^1$H-NMR spectra, to be identical to a sample obtained according to Example 34.

EXAMPLE 47

5,11-Dihydro-11-[[2-[(dimethylamino)methyl]-1-piperidinyl]acetyl]-6H-pyrido[2,3-b][1,4]benzodiazepin-6-one The title compound is prepared analogously to Example 46 from 2-[(dimethylamino)methyl]-1-piperidinoacetic acid and 5,11-dihydro-6H-pyrido[2,3-b][1,4]benzodiazepin-6-one. Colorless crystals, mp. 189°–190° C. (n-propanol), are shown by thin layer chromatography, mixed melting point and IR spectrum to be identical to a sample obtained according to Example 5.

EXAMPLE 48

11-[[2-[(Diethylamino)methyl]-1-piperidinyl]acetyl]-5,11-Dihydro-6H-pyrido[2,3-b][1,4]benzodiazepin-6-one Ethyl chlorocarbonate (11.0 g, 0.101 mol) is added dropwise, at 0° C., to a suspension of 2-[(diethylamino)-methyl]-1-piperidino acetic acid (22.83 g, 0.1 mol) in dry tetrahydrofuran (200 ml). Then, 5,11-dihydro-6H-pyrido[2,3-b][1,4]benzodiazepin-6-one (21.12 g, 0.1 mol) and triethylamine (20.24 g, 0.2 mol) are added to the resulting suspension which is then stirred for a further hour at 0° C. and then for 4 hours at ambient temperature. The mixture is poured into 2N sodium hydroxide solution (1.6 liters), extracted exhaustively with dichloromethane, the organic phase concentrated to dryness and the residue purified by recrystallization from ethanol and from methanol. Colorless crystals (6.3 g) are obtained, mp. 226°–228° C., which were shown by thin layer chromatography, mixed melting point and IR spectrum to be identical to a sample prepared according to Example 34.

EXAMPLE 49

4-[[2-[(Dimethylamino)methyl]-1-piperidinyl]acetyl]-1-methyl-1,4,9,10-tetrahydropyrrolo[3,2-b][1,5]benzodiazepin-10-one First, 3-chloro-4-[[2-[(dimethylamino)methyl]-1-piperidinyl]acetyl]-1-methyl-1,4,9,10-tetrahydropyrrolo[3,2-b][1,5]benzodiazepin-10-one (4.17 g, 9.7 mmol) is dissolved in a mixture of 85% formic acid (5 ml) and dimethylformamide (25 ml) and, after the addition of 10% palladium/activated charcoal (0.5 g), the mixture is refluxed for 3 hours. Formic acid (7.0 ml) is added, the mixture is refluxed for 6 hours, additional formic acid (4.0 ml) and 10% palladium/activated charcoal (0.8 g) are added, and the mixture is finally refluxed for a further 8 hours. The mixture is filtered while hot, the filtrate is concentrated in vacuo and the residue is purified by column chromatography (silica gel; dichloromethane/ethyl acetate/methanol/conc. ammonia 3.5:1.5:0.46:0.06 v/v). Colorless crystals (1.3 g) are obtained, mp. 163°–165° C. (acetonitrile), which are shown by thin layer chromatography and IR, UV and $^1$H-NMR spectra, to be identical to a preparation obtained according to Example 3.

EXAMPLE 50

4-[[2-[(Diethylamino)methyl]-1-piperidinyl]acetyl]-1-methyl-1,4,9,10-tetrahydropyrrolo[3,2-b][1,5]benzodiazepin-10-one A mixture of 3-chloro-4-[[2-[(diethylamino-)methyl]-1-piperidinyl]acetyl]-1-methyl-1,4,9,10-tetrahydropyrrolol[3,2-b][1,5]benzodiazepin-10-one (4.58 g, 0.01 mol), 2,1-tris(o-tolyl)-phosphine-palladium acetate catalyst (83.3 mg, 0.001 mol), formic acid (2.025 g, 0.044 mol) and triethylamine (5.77 g, 0.057 mol) in tetrahydrofuran (200 ml) is heated to 100° C. in an autoclave under a nitrogen atmosphere for 40 hours. The mixture is filtered and concentrated in vacuo, and the residue is made alkaline with sodium hydroxide and extracted exhaustively with dichloromethane. The dried and concentrated organic phases are purified by column chromatography as in Example 49. Colorless crystals (1.55 g) are obtained, mp. 141°–144° C. (acetonitrile), which are shown by thin layer chromatography and IR spectrum to be identical to a sample obtained according to Example 4.

EXAMPLE 51

(S)-5,11-Dihydro-11-[[2-[(4-morpholinyl)methyl]-1-pyrrolidinyl]-acetyl]-6H-pyrido[2,3-b][1,4]benzodiazepin-6-one The title compound is prepared analogously to Example 31 from 11-(chloroacetyl)-5,11-dihydro-6H-pyrido[2,3-b][1,4]benzodiazepin-6-one and (S)-4-[(2-pyrrolidinyl)methyl]morpholine to give colorless crystals, mp. 202°–203° C. (ethyl acetate/methanol 1:1 v/v); $[\alpha]_D^{20} = -2.93°$ C. (ethanol).

EXAMPLE 52

(+)-11-[[2-[(Diethylamino)methyl]-1-piperidinyl]acetyl]-5,11-dihydro-6H-pyrido[2,3-b][1,4]benzodiazepin-6-one (a) (−)-2-[(Diethylamino)methyl]piperidine Solutions of racemic 2-[(diethylamino)methyl]piperidine (45.2 g, 0.265 mol) in methanol (132 ml) and L-(+)-tartaric acid (93.0 g, 0.62 mol) in methanol (264 ml) are combined, the mixture is left to stand overnight at ambient temperature and the precipitate so formed is suction filtered, washed with methanol and decanted with methanol (250 ml) for 30 minutes. The mixture is recrystallized from ethanol/water (4:1 v/v) four times in all and colorless crystals (29.9 g) are obtained, mp. 191°–192.5° C., which are identified as the ditartrate.

Elemental Analysis for $C_{10}H_{22}N_2 \cdot 2C_4H_6O_6$: Calculated: C, 45.95; H, 7.28; N, 5.95. Found: C, 46.06; H, 7.08; N, 5.96.

The product is reacted with potassium hydroxide solution and, after the usual working up, the desired free base is obtained, boiling point $_{17\ mm\ Hg}$ 88°–94° C.; $[\alpha]_D^{20}$ −68° (ethanol).

In order to determine the content, a sample of the base is converted with (S)-(−)-1-phenylethyl isocyanate into the corresponding urea and subsequently investigated using HPLC. The content in the base of (−)-enantiomer according to this is at least 98.9%.

(b)

(+)-11-[[2-[(Diethylamino)methyl-]-1-piperidinyl]acetyl]-5,11-dihydro-6H-pyrido[2,3-b][1,4]benzodiazepin-6-one The title compound is prepared analogously to Example 2 from 11-(chloroacetyl)-5,11-dihydro-6H-pyrido[2,3-b][1,4]benzodiazepin-6-one and (−)-2-[(diethylamino)methyl]piperidine to give colorless crystals, mp. 210°–211.5° C. (n-propanol; $[\alpha]_D^{20} = +11.4°$ (dilute aqueous hydrochloric acid). The dihydrobromide melts at 241°–242° C. (with decomposition; from ethanol).

EXAMPLE 53

(−)-11-[[2-[(Diethylamino)methyl]-1-piperidinyl]acetyl]-5,11-Dihydro-6H-pyrido[2,3-b][1,4]benzodiazepin-6-one (a) (+)-2-[(Diethylamino)methyl]piperidine The title compound is prepared analogously to Example 52(a) from racemic 2-[(dimethylamino)methyl]piperidine and D-(−)-tartaric acid. The ditartrate melted at 191°–192.5° C. The base, with a boiling point $_{17\ mm\ Hg}$ 88°–94° C., had a content of (+)-enantiomer determined by reaction with (S)-(−)-1-phenylethylisocyanate and subsequent HPLC investigation, of 98.5%. $[\alpha]_D^{20} = +64°$ (ethanol).

(b)

(−)-11-[[2-[(Diethylamino)methyl]-1-piperidinyl]acetyl]-5,11-dihydro-6H-pyrido[2,3-b][1,4]benzodiazepin-6-one The title compound is prepared analogously to Example 2 from 11-(chloroacetyl)-5,11-dihydro-6H- pyrido[2,3-b][1,4]benzodiazepin-6-one and (+)-2-[(diethylamino)methyl]piperidine to give colorless crystals, mp. 210°–211.5° C. (n-propanol/activated charcoal): [α]$_D^{20}$=−12° (dilute aqueous hydrochloride acid).

EXAMPLE 54

11-[[3-(Diethylamino)-hexahydro-1H-azepin-1-yl]acetyl]-5,11-dihydro-6H-pyrido[2,3-b][1,4]benzodiazepin-6-one The title compound is prepared analogously to Example 2 from 11-(chloroacetyl)-5,11-dihydro-6H-pyrido[2,3-b][1,4]benzodiazepin-6-one and 3-(diethylamino)-hexahydro-1H-azepine to give colorless crystals, mp. 222°–224° C. (n-propanol).

EXAMPLE 55

4-[[2-[(Diethylamino)methyl]-1-piperidinyl]acetyl]-4,9-dihydro-3-methyl-10H-thieno[3,4-b][1,5]benzodiazepin-10-one The title compound is prepared analogously to Example 2 from 4-(chloroacetyl)-4,9-dihydro-3-methyl-10H-thieno[3,4-b][1,5]benzodiazepin-10-one and 2-(diethylamino)methyl]piperidine to give colorless crystals, mp. 147°–149° C. (cyclohexane/ethyl acetate 9:1 v/v).

EXAMPLE 56

4,9-Dihydro-4-[[2-[(dimethylamino)methyl]-1-piperidinyl]-acetyl]-3-methyl-10H-thieno[3,4-b][1,5]benzodiazepin-10-one The title compound is prepared analogously to Example 2 from 4-(chloroacetyl)-4,9-dihydro-3-methyl-10H-thieno[3,4-b][1,5]benzodiazepin-10-one and 2-(dimethylamino)methyl]piperidine to give colorless crystals, mp. 172°–173° C. (cyclohexane/ethyl acetate 4:1 v/v).

EXAMPLE 57

11-[[2-[(Diethylamino)methyl]-1-piperidinyl]acetyl]-5,11-Dihydro-6H-pyrido[2,3-b][1,4]benzodiazepin-6-one A suspension of 11-(chloroacetyl)-5,11-dihydro-6H-pyrido[2,3-b][1,4]benzodiazepin-6-one (276 g, 0.959 mol), and 2-[(diethylamino)methyl]piperidine dihydrochloride (244.95 g, 100.7 mol), of sodium carbonate (223.9 g, 2.112 mol) and acetonitrile (1.92 liters) are stirred for 6 hours at a reaction temperature of 70° C. After this time, the 11-(chloroacetyl)-5,11-dihydro-6H-pyrido[2,3-b][1,4]benzodiazepin-6-one has 95-97% reacted (TLC). The mixture is left to stand overnight at ambient temperature, then suction filtered. The contents of the filter are washed three times, each time with acetonitrile (60 ml). The dark colored filtrates are discarded. The remaining solid is stirred for a further 2 hours with water (1.5 liters), suction filtered again and washed with another water (300 ml) and finally dried at 40° C. in a circulating air drier. The crude product thus obtained (390 g) is transferred into a 10 liter flask, taken up in 1-propanol (5.14 liters) and, after the addition of 2-[(diethylamino)methyl]piperidine dihydrochloride (13.5 g, 0.0555 mol) and anhydrous sodium carbonate (11.8 g, 0.1113 mol), refluxed for 16 hours. After the addition of activated charcoal (39 g) the mixture is heated to boiling for a further 30 minutes and the boiling hot mixture is then forced through a SEITZ filter. Clarification is repeated twice more in the same way using activated charcoal (20 g). The filtrate is left to stand for 12 hours at ambient temperature, the precipitated crystals are suction filtered and washed twice, each time with 1-propanol (50 ml). The product is again stirred with cold 1-propanol (0.5 liters), suction filtered and again washed twice, each time with 1-propanol (50 ml). It is then dried in a circulating air drier at 40° C. and almost colorless crystals (263 g) are obtained, mp. 226°–227° C.

EXAMPLE 58

5,10-Dihydro-5-[[3-(1-methyl-2-pyrrolidinyl)-1-piperidinyl]acetyl]-11H-dibenzo[b,e][1,4]diazepin-11-one The title compound is prepared analogously to Example 35 from 5-(chloroacetyl)-5,10-dihydro-11H-dibenzo[b,e][1,4]diazepin-11-one and hexahydronicotine to give colorless crystals, mp. 161°–163° C. (ethyl acetate).

EXAMPLE 59

5,11-Dihydro-11-[[3-(1-methyl-2-pyrrolidinyl)-1-piperidinyl]acetyl]-6H-pyrido[2,3-b][1,4]benzodiazepin-6-one The title compound is prepared analogously to Example 35 from 11-(chloroacetyl)-5,11-dihydro-6H-pyrido[2,3-b][1,4]benzodiazepin-6-one and hexahydronicotine to give colorless crystals, mp. 203° C. (diisopropyl ether).

EXAMPLE 60

5-[[3-[[Cyclohexyl)(methyl)amino]methyl]-1-piperidinyl]acetyl]-5,10-dihydro-11H-dibenzo[b,e]-[1,4]diazepin-11-one The title compound is prepared analogously to Example 35 from 5-(chloroacetyl)-5,10-dihydro-11H-dibenzo[b,e][1,4]diazepin-11-one and 3-[[(cyclohexyl)(methyl)amino]methyl]piperidine to give colorless crystals, mp. 195°–196° C. (ethyl acetate/1,2-dichloroethane/diisopropyl ether 1:1:1 v/v/v).

EXAMPLE 61

11-[[3-[[(Cyclohexyl)(methyl)amino]methyl]-1-piperidinyl]acetyl]-5,11-dihydro-6H-pyrido[2,3-b][1,4]benzodiazepin-6-one The title compound is prepared analogously to Example 35 from 11-(chloroacetyl)-5,11-dihydro-6H-pyrido[2,3-b][1,4]benzodiazepin-6-one and 3-[[(cyclohexyl)(methyl)amino]methyl]piperidine to give colorless crystals, mp. 199°–200° C. (diisopropylether).

EXAMPLE 62

5,10-Dihydro-5-[[3-[(dimethylamino)methyl]-1-piperidinyl]-acetyl]-11H-dibenzo[b,e][1,4]diazepin-11-one The title compound is prepared analogously to Example 35 from 5-(chloroacetyl)-5,10-dihydro-11H-dibenzo[b,e][1,4]diazepin-11-one and 3-[[(dimethylamino)methyl]piperidine to give colorless crystals, mp. 148°–150° C. (diisopropyl ether).

EXAMPLE 63

5,11-Dihydro-11-[[3-[(dimethylamino)methyl]-1-piperidinyl]-acetyl]-6H-pyrido[2,3-b][1,4]benzodiazepin-6-one The title compound is prepared analogously to Example 35 from 11-(chloroacetyl)-5,11-dihydro-6H- pyrido[2,3-b][1,4]benzodiazepin-6-one and 3-[(dimethylamino)methyl]piperidine to give colorless crystals, mp. 189°–190° C. (diisopropyl ether).

EXAMPLE 64

5,10-Dihydro-5-[[3-[(1-pyrrolidinyl)methyl]-1-piperidinyl]-acetyl]-11H-dibenzo[b,e][1,4]diazepin-11-one The title compound is prepared analogously to Example 35 from 5-(chloroacetyl)-5,10-dihydro-11H-dibenzo[b,e][1,4]diazepin-11-one and 3-[(1-pyrrolidinyl)methyl]piperidine to give colorless crystals, mp. 145°–146° C. (ethyl acetate/diisopropyl ether 1:1 v/v).

EXAMPLE 65

5,11-Dihydro-11-[[3-(1-pyrrolidinyl)-1-piperidinyl]acetyl]-6H-pyrido[2,3-b][1,4]benzodiazepin-6-one The title compound is prepared analogously to Example 35 from 11-(chloroacetyl)-5,11-dihydro-6H-pyrido[2,3-b][1,4]benzodiazepin-6-one and 3-[(1-pyrrolidinyl)methyl]piperidine to give colorless crystals, mp. 174°–176° C. (diisopropyl ether).

EXAMPLE 66

5,11-Dihydro-[11-[[(1-piperidinyl)methyl]-1-piperidinyl]acetyl]-6H-pyrido[2,3-b][1,4]benzodiazepin-6-one The title compound is prepared analogously to Example 35 from 11-(chloroacetyl)-5,11-dihydro-6H-pyrido[2,3-b][1,4]benzodiazepin-6-one and 3-[(1-piperidinyl)methyl]piperidine to give colorless crystals, mp. 188°–190° C. (ethyl acetate/diisopropyl ether 1:1 v/v).

EXAMPLE 67

5,10-Dihydro-5-[[3-[(1-piperidinyl)methyl]-1-piperidinyl]-acetyl]-11H-dibenzo[b,e][1,4]diazepin-11-one The title compound is prepared analogously to Example 35 from 5-(chloroacetyl)-5,10-dihydro-11H-dibenzo[b,e][1,4]diazepin-11-one and 3-[(1-piperidinyl)methyl]piperidine to give colorless crystals, mp. 150°–152° C. (ethyl acetate).

EXAMPLE 68

11-[[2-[(Diethylamino)methyl]-hexahydro-1H-azepin-1yl]-acetyl]-5,11-dihydro-6H-pyrido[2,3-b][1,4]benzodiazepin-6-one The title compound is prepared analogously to Example 35 from 11-(chloroacetyl)-5,11-dihydro-6H-pyrido[2,3-b][1,4]benzodiazepin-6-one and 2-[(diethylamino)methyl]-hexahydro-1H-azepine to give colorless crystals, mp. 151°–153° C. (diisopropyl ether/ethyl acetate).

EXAMPLE 69

5-[[2-[(Diethylamino)methyl]-hexahydro-1H-azepin-1-yl]-acetyl]-5,10-dihydro-11H-dibenzo[b,e][1,4]diazepin-11-one The title compound is prepared analogously to Example 35 from 5-(chloroacetyl)-5,10-dihydro-11H-dibenzo[b,e][1,4]diazepin-11-one and 2-[(diethylamino)methyl]-hexahydro-1H-azepine to give colorless crystals, mp. 118°–120° C. (diisopropyl ether).

EXAMPLE 70

5,11-Dihydro-11-[[2-[(dimethylamino-N-oxide)methyl]-1-piperidinyl]acetyl]-6H-pyrido[2,3-b][1,4]benzodiazepin-6-one First, 35% perhydrol (1 ml) is added dropwise to a solution of 5,11-dihydro-11-[[2-[(dimethylamino)methyl]-1-piperidinyl]acetyl]-6H-pyrido[2,3-b][1,4]benzodiazepin-6-one (1.5 g, 3.81 mmol) in methanol (10 ml) and stirred for 6 hours at 30° C. The excess hydrogen peroxide is decomposed by addition of a trace of platinum black and, after filtration, the solution is concentrated and the residue is purified by chromatograph on kieselgel (100 g) using as eluant methylene chloride/methanol/cyclohexane/concentrated ammonia in a ratio by volume of 68:15:15:2. After concentrating the corresponding eluate and crystallization from ethyl acetate and then acetonitrile, colorless crystals (0.6 g) are obtained, mp. 171°–172° C.

EXAMPLE 71

11-[[2-[(Diethylamino-N-oxide)methyl]-1-piperidinyl]-acetyl]-5,11-dihydro-6H-pyrido[2,3-b][1,4]benzodiazepin-6-one The title compound is prepared analogously to Example 70 from 11-[[2-[(dimethylamino)methyl]-1-piperidinyl]-5,11-dihydro]-6H-pyrido[2,3-b][1,4]benzodiazepin-6-one and hydrogen peroxide to give colorless crystals, mp. 186°–187° C. (acetonitrile).

EXAMPLE 72

A. Investigation of functional selectivity of the antimuscarinic activity

Substances having antimuscarinic properties inhibit the effects of agonists supplied exogenously or of acetylcholine released from cholinergic nerve endings. The following are descriptions of methods which are suitable for testing cardioselective antimuscarinic agents.

"In vitro" organ preparations

Dissociation constants ($K_B$ values) are measured "in vitro" in the ileum and electrically stimulated auricle of guinea pigs. The ileum is removed and incubated in Tyrode's solution in an organ bath. Contractions are produced by increasing concentrations of bethanechol (B) so that complete concentration-activity curves can be plotted. Then the B is washed out, the test substance is added and left in contact for 2 minutes and again the concentration-activity curve is plotted with B.

The dissociation constant is calculated according to Arunlakshana and Schild (*Brit. J. Pharmacol.*, 14:48, 1959) from the dosage ratio (DR), i.e. the extent of shift of the concentration-activity curve.

In the isolated, electrically stimulated left auricle, B reduces the contractile force as a function of the concentration. This effect is reversed by the administration of an antimuscarinic agent. Dissociation constants for the muscarinic receptors of the auricle are obtained in the same way as described above. A comparison of the dissociation constants obtained in both tissues makes it possible to identify cardioselective substances.

"In vivo" methods

The methods used have the objective of confirming the selectivity of the antimuscarinic acitivity. Those substances which are selected on the basis of "in vitro" investigations are tested for:
1. tachycardiac effect in conscious dogs;
2. inhibitory effect on gastric acid secretion in pylorous-ligated rats; and
3. mydriatic effect in rats.

1. Heart rate increasing activity in the conscious dogs

The substances are injected intravenously and the heart rate is measured with the aid of a tachygraph. After a control period, increasing doses of the compound are administered in order to increase the heart rate. The next dose is injected when the effect of the preceding dose is no longer visible. The dosage of a substance which brings about an increase of 50 beats per minute ($ED_{50}$) is determined graphically. Each substance is tested on 3 to 5 dogs.

2. Inhibition of secretion in rats

The method described by Shay et al. (Gastroenterology, 26, 906, 1954) is used. Increasing doses of the substance are injected intravenously into male Wistar rats (10 rats per group) 5 minutes before the ligature of the pylorus. The rats are killed 2 hours later and both the volume of gastric acid and also the "acid output" are determined by titration. The dosage of substance which reduces either the volume or the acid output by 50% is determined.

3. Mydriatic activity in rats

The mydriasis is determined, after intravenous injection of the test substance, by measuring the increase in pupil size. The pupil size is measured using a microscope. The measurements are taken before and at various times (15, 45 and 75 minutes) after the injection of various doses of the substance. The results were expressed in terms of the $ED_{200}$. This is the dose which effects a doubling in the diameter of the pupil, relative to the base value. The maximum effect is generally observed between 15 and 45 minutes after intravenous administration.

B. Studies of binding to muscarinic receptors: determining the $IC_{50}$ value

The organ donors are Sprague-Dawley rats weighing from 180–220 g. After the removal of the heart, stomach and cerebral cortex, all the other steps are carried out in ice-cold Hepes-HCl buffer (pH 7.4; 100 m molar NaCl, 10 m molar $MgCl_2$). The whole heart is cut up with scissors. All the organs are then homogenised in a Potter apparatus. For the bonding test, the homogenised organs are diluted as follows:
whole heart 1:250
cerebral cortex 1:3000

The homogenised organs are incubated at a specific concentration of the radioligand and with a series of concentrations of the non-radioactive test substances in an Eppendorf centrifugal test tube at 30° C. Incubation lasts 45 minutes. The radioligand is 0.3 n molar $^3$H-N-methylscopolamine ($^3$H-NMS). After incubation has been ended by centrifuging at 14,000 g, the radioactivity in the pellet is determined. It represents the sum of specific and non-specific binding of $^3$H-NMS. The proportion of non-specific binding is defined as the radioactivity which binds in the presence of 1 μmolar quinuclidinyl benzylate. Four measurements are made in each case. The $IC_{50}$ values of the non-labeled test substances are determined graphically. They represent the concentration of test substance at which the specific binding of $^3$H-NMS to the muscarinic receptors in the various organs is inhibited by 50%.

The following compounds are tested, by way of example, in accordance with the methods described above:

A = 11-[[2-[(Diethylamino)methyl]-1-piperidinyl]-acetyl]-5,11-dihydro-6H-pyrido[2,3-b][1,4]benzodiazepin-6-one B = 5,11-Dihydro-11-[(4-methyl-1-piperazinyl)acetyl]-6H-pyrido[2,3-b][1,4]benzodiazepin-6-one (pirenzepine)

C = Atropine

D = 5,11-Dihydro-11-[[[2-(dimethylamino)methyl]-1-piperidinyl]acetyl]-6H-purido[2,3-b][1,4]benzodiazepin-6-one E = 5,11-Dihydro-11-[[2-[2-(dimethylamino)ethyl]-1-piperidinyl]acetyl]-6H-pyrido[2,3-b][1,4]benzodiazepin-6-one F = 5-[[2-[(Diethylamino)methyl]-1-piperidinyl]acetyl]-5,10-dihydro-11H-dibenzo[b,e][1,4]diazepin-11-one G = 4-[[2-[(Diethylamino)methyl]-1-piperidinyl]acetyl]-4,9-dihydro-10H-thieno[3,4-b][1,4]benzodiazepin-10-one H = (S)-11-[[2-[(Diethylamino)methyl]-1-pyrrolidinyl]-acetyl]-5,11-dihydro-6H-pyrido[2,3-b][1,4]benzodiazepin-6-one I = (S)-5[[2-[(Diethylamino)methyl]-1-pyrrolidinyl]-acetyl]-5,10-dihydro-11H-dibenzo[b,e][1,4]diazepin-11-one K = trans-5,11-Dihydro-11-[[2-[[(4-hydroxycyclohexyl)-(methyl)amino]methyl]-1-piperidinyl]acetyl]-6H-pyrido[2,3-b][1,4]benzodiazepin-6-one L = 11-[[3-[[(Cyclohexyl)(methyl)amino]-1-piperidinyl]acetyl]-5,11-dihydro]-6H-pyrido[2,3-b][1,4]benzodiazepin-6-one M = 5-[[3-[(Diethylamino)methyl]-1-piperidinyl]acetyl]-5,10-dihydro-11H-dibenzo[b,e][1,4]diazepin-11-one N = 5-[[2-[[(Cyclohexyl)methyl)amino]methyl]-1-piperidinyl]acetyl]-5,10-dihydro-11H-dibenzo[b,e][1,4]diazepin-11-one O = 5-[[3-[[(Cyclohexyl)(methyl)amino]methyl]-1-piperidinyl]-acetyl]-5,10-dihydro-11H-dibenzo[b,e][1,4]diazepin-11-one P = 5,10-Dihydro-5-[[3-(1-methyl-2-pyrrolidinyl)-1-piperidinyl]acetyl]-11H-dibenzo[b,e][1,4]diazepin-11-one Q = 11-[[2-[(Butylmethylamino)methyl]-1-piperidinyl]-acetyl]-5,10-dihydro-11H-dibenzo[b,e][1,4]diazepin-11-one

TABLE 1

| Substance | Receptor binding tests $IC_{50}[nMl^{-1}]$ Cortex | Heart |
|---|---|---|
| A | 1200 | 140 |
|  | 3000 | 150 |
| B | 100 | 1500 |
| C | 2 | 4 |
| D | 1500 | 150 |
|  |  | 130 |
| E | 1300 | 170 |
| F | 750 | 150 |
|  | 1000 | 100 |
| G | 2200 | 220 |
| H | 4500 | 400 |
| I | 800 | 90 |
| K | 1100 | 70 |
| L | 85 | 19 |
| M | 100 | 35 |
| N | 50 | 13 |
| O | 20 | 2.8 |
| P | 120 | 17 |

TABLE 1-continued

| | Receptor binding tests | |
|---|---|---|
| | $IC_{50}[nMl^{-1}]$ | |
| Substance | Cortex | Heart |
| Q | 100 | 18 |

The results in Table 1 above show that the new compounds of formula I distinguish between muscarinic receptors in different tissues. This is clear from the considerably lower $IC_{50}$ values when the tests are carried out on preparations of cerebral cortex as opposed to those from the smooth muscle of the stomach and heart.

TABLE 2

| Substance | Tachycardia (dog) $ED_{50}[\mu g/kg]$ i.v. | Inhibition of secretion (Shay rat) $ED_{50}[\mu g/kg]$ i.v. | Mydriasis (rat) $ED_{50}[\mu g/kg]$ i.v. |
|---|---|---|---|
| A | 103 | >10000 | >3000 |
| B | 468 | 400 | 408 |
| C | 7.7 | 31 | 4 |

The pharmacological data in Table II above show (in full agreement with the receptor binding studies) that the heart rate is increased by the above-mentioned compounds even at dosages in which there is no restriction in gastric acid secretion and no mydriasis.

The preparation of some pharmaceutical formulations will now be described by way of example:

EXAMPLE I

Tablets containing 11-[[2-[(diethylamino)methyl]-1-piperidinyl]acetyl]-5,11-dihydro-6H-pyrido[2,3-b]-benzodiazepin-6-one

| Composition: | |
|---|---|
| 1 Tablet contains: | |
| Active substance | 5.0 mg |
| Lactose | 148.0 mg |
| Potato starch | 65.0 mg |
| Magnesium stearate | 2.0 mg |
| | 220.0 mg |

Preparation

A 10% musilage is prepared from potato starch by heating. The active substance, lactose and remaining potato starch are mixed together and granulated with the above musilage through a screen with a mesh size of 1.5 mm. The granulate is dried at 45° C., passed through the above screen once more, mixed with magnesium stearate and compressed to form tablets.
Weight of tablet: 220 mg
Punch: 9 mm

EXAMPLE II

Coated tablets containing 11-[[2-[(diethylamino)methyl]-1-piperidinyl]acetyl]-5,11-dihydro-6H-pyrido-[2,3-b][1,4]benzodiazepin-6-one The tablets prepared in Example I are coated in known manner with a coating consisting essentially of sugar and talc. The finished coated tablets are polished with beeswax.
Weight of coated tablet: 300 mg.

EXAMPLE III

Ampoules containing 11-[[2-[(diethylamino)methyl]-1-piperidinyl]acetyl]-5,11-dihydro-6H-pyrido[2,3-b]-[1,4]benzodiazepin-6-one

| Composition: | |
|---|---|
| 1 Ampoule contains: | |
| Active substance | 1.0 mg |
| Sodium chloride | 8.0 mg |
| Distilled water ad. | 1 ml |

Preparation

The active substance and sodium chloride are dissolved in distilled water and then made up to the volume specified. The solution is filtered sterile and transferred into 1 ml ampoules. Sterilization: 20 minutes at 120° C.

EXAMPLE IV

Suppositories containing 11-[[2-[(diethylamino)methyl]-1-piperidinyl]acetyl]5,11-dihydro-6H-pyrido-[2,3-b][1,4]benzodiazepin-6-one

| Composition: | |
|---|---|
| 1 Suppository contains: | |
| Active substance | 5.0 mg |
| Suppository mass (e.g. Witepsol W 45 ®) | 1,695.0 mg |
| | 1,700.0 mg |

Preparation

The finely powdered active substance is suspended in the molten suppository mass which has been cooled to 40° C. At 37° C. the mass is poured into slightly chilled suppository moulds. Weight of suppository: 1.7 g

EXAMPLE V

Drops containing 4,9-dihydro-11[[2-[(diethylamino)methyl]-1-piperidinyl]acetyl]-5,11-dihydro-6H-pyrido[2,3-b][1,4]benzodiazepin-6-one

| Composition: | |
|---|---|
| 100 ml of drop solution contain: | |
| methyl p-hydroxybenzoate | 0.035 g |
| propyl p-hydroxybenzoate | 0.015 g |
| Anisole | 0.05 g |
| Menthol | 0.06 g |
| Pure ethanol | 10.0 g |
| Active substance | 0.5 g |
| Sodium cyclamate | 1.0 g |
| Glycerol | 15.0 g |
| Distilled water ad | 100.0 ml |

Preparation

The active substance and sodium cyclamate are dissolved in about 70 ml of water and glycerol is added. The p-hydroxy-benzoates, anisole and menthol are dissolved in ethanol and this solution is added to the aqueous solution with stirring. Finally the solution is made up to 100 ml with water and filtered to remove any suspended particles.

What is claimed is:

1. A compound having the formula

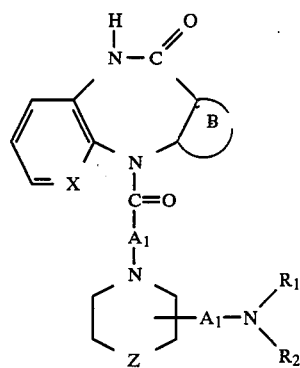

wherein
B is a fused ring selected from

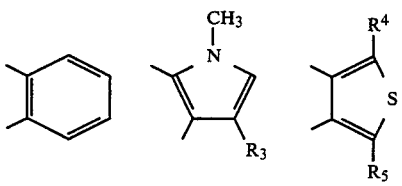

X is —CH— or, when B is ortho-phenylene, it can alternatively be nitrogen;

$A_1$ is $C_1$–$C_2$ alkylene;

$A_2$ is $C_1$–$C_2$ alkylene when it is in the 2-position relative to the saturated heterocyclic ring nitrogen or a single bond or methylene, when it is in the 3- or 4-position;

$R_1$ is $C_1$–$C_3$ alkyl;

$R_2$ is $C_1$–$C_7$ alkyl, optionally hydroxy substituted on at least one of its second to seventh carbon, or $C_3$–$C_7$ cycloalkyl, optionally hydroxy substituted, or $C_3$–$C_7$ cycloalkylmethyl; or $R_1$ and $R_2$ can, together with the nitrogen therebetween, be a 4- to 7- membered saturated, monocyclic, heterocyclic ring which can optionally include an oxygen or N—$CH_3$;

$R_3$ is hydrogen, chlorine or methyl;

$R_4$ is hydrogen or $C_1$–$C_4$ alkyl;

$R_5$ is hydrogen, chlorine, or $C_1$–$C_4$ alkyl and

Z is a single bond, oxygen, methylene or 1,2-ethylene group, the diastereoisomers and enantiomers thereof and the $NR_1R_2$-N oxides and physiologically acceptable acid addition salts thereof with inorganic or organic acids.

2. A compound of general formula I according to claim 1 wherein $R_1$ to $R_3$ and X are defined as in claims 1, Z is a single bond or a methylene group, $A_1$ and $A_2$ each represents a methylene group, $R_4$ represents a hydrogen atom or a methyl group and $R_5$ represents a hydrogen or chlorine atom or a methyl group, the diastereoisomers and enantiomers thereof and the $NR_1R_2$-N-oxides and physiologically acceptable acid addition salts thereof with inorganic or organic acids.

3. A compound of general formula I according to claim 1, wherein

X is defined as in claims 1,

Z represents a single bond or a methylene group,

B represents a ortho-phenylene group or a 3,4-linked thieno group, $A_1$ represents a methylene group, $A_2$ represents a methylene group in the 2-position relative to the N-atom of the saturated heterocyclic ring, $R_1$ represents a methyl or ethyl group and $R_2$ represents a methyl, ethyl or 4-hydroxycyclohexyl group, the diastereoisomers and enantiomers thereof and the $NR_1R_2$-N-oxides and physiologically acceptable acid addition salts thereof with inorganic or organic acids.

4. 11-[[2-[(Diethylamino)methyl]-1-piperidinyl]-acetyl]-5,11-dihydro-6H-pyrido[2,3-b][1,4]benzodiazepin-6-one.

5. trans-5,11-Dihydro-11-[[2-[[(4-hydroxycyclohexyl)-(methyl)amino]methyl]-1-piperidinyl]acetyl]-6H-pyrido[2,3-b][1,4]benzodiazepin-6-one.

6. 5,11-Dihydro-11-[[[2-(dimethylamino)methyl]-1-piperidinyl]acetyl]-6-pyrido[2,3-b][1,4]benzodiazepin-6-one.

7. (S)-11-[[2-[(Diethylamino)methyl]-1-pyrrolidinyl]-acetyl]-5,11-dihydro-6H-pyrido[2,3-b][1,4]benzodiazepine-6-one.

8. A pharmaceutical composition for the treatment of bradycardia in a mammal which comprises an effective amount of a compound of any of claims 1 to 7 and a nontoxic, pharmaceutically acceptable carrier.

9. A pharmaceutical composition for the treatment of bradyarrhythmia in a mammal which composition comprises an effective amount of a compound of any of claims 1 to 7 and a nontoxic, pharmaceutically acceptable carrier.

10. A method of treating bradycardia in a mammal in need thereof which comprises administering an effective amount of a compound of any of claims 1 to 7 to said mammal.

11. A method of treating bradyarrhythmia in a mammal in need thereof which comprises administering an effective amount of a compound of any of claims 1 to 7 to said mammal.

* * * * *